(12) United States Patent
Ueno et al.

(10) Patent No.: US 6,878,371 B2
(45) Date of Patent: Apr. 12, 2005

(54) THERAPEUTIC ANGIOGENESIS BY BONE MARROW-DERIVED CELL TRANSPLANTATION IN MYOCARDIAL ISCHEMIC TISSUE AND SKELETAL MUSCLE ISCHEMIC TISSUE

(75) Inventors: Takafumi Ueno, Decatur, GA (US); Toyoaki Murohara, Fukuoka (JP); Keith Allen Robinson, Norcross, GA (US); Nicolas A. F. Chronos, Atlanta, GA (US); Sam Baldwin, Newton, MA (US); Maria Palasis, Wellesley, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days.

(21) Appl. No.: 09/915,853

(22) Filed: Jul. 26, 2001

(65) Prior Publication Data

US 2002/0037278 A1 Mar. 28, 2002

Related U.S. Application Data

(60) Provisional application No. 60/220,834, filed on Jul. 26, 2000.

(51) Int. Cl.$^7$ .............................. G09B 25/08; C12N 5/00
(52) U.S. Cl. ..................... 424/93.1; 424/93.7; 435/325
(58) Field of Search ............................... 435/93.1, 325; 424/93.1, 93.7

(56) References Cited

FOREIGN PATENT DOCUMENTS

WO    WO 01/20999    3/2001

OTHER PUBLICATIONS

Kobayashi et al (J. Surgical Res. Apr. 2000; 89(2):189–95).*
Prockop D (Science 1997; 276:71–74).*
Hamano, K. et al. "The Induction of angiogenesis by the implantation of autologus bone marrow cells: A novel and simple therapeutic method", Surgery, Jul. 2001, vol. 130, No. 1, pp. 44–54.

Kalka, C. et al. "Transplantation of ex vivo expanded endothelial progenitor cells for therapeutic neovascularization", PNAS, Mar. 28, 2000, vol. 97, No. 7, pp. 3422–3427.

Shintani S., et al., "Local transplantation of Autologus bone marrow–derived mononuclear cells augments collateral vessel formation in ischemic hindlimb in rabbits", Circulation, Nov. 2, 1999, vol. 100, No. 18, p. I.406, Abstract.

Ueno, T. et al., "Therapeutic angiogenesis by bone marrow–derived cell transplantation in pigs with coronary constrictor–induced chronic myocardial ischemia", J Am Col Cardiol, Feb., 2001, vol. 37, No. 2, Supplement A, p. 48A, Abstract.

* cited by examiner

*Primary Examiner*—G. Nickel
*Assistant Examiner*—C. Yaen
(74) *Attorney, Agent, or Firm*—Kenyon & Kenyon

(57) ABSTRACT

This invention provides methods of forming new blood vessels in diseased or damaged tissue in a subject, methods of increasing blood flow to diseased or damaged tissue in a subject, and methods of increasing angiogenesis in diseased tissue in a subject, which methods comprise: a) isolating autologous bone marrow-mononuclear cells from the subject; and b) transplanting locally into the diseased or damaged tissue an effective amount of the autologous bone-marrow mononuclear cells, thereby forming new blood vessels in the diseased or damaged tissue. The new blood vessels may be capillaries or collateral vessels in ischemic tissue or any site of angiogenesis. Also provided are methods of treating tissue in disease or injury by local transplantation with an effective amount of the autologous bone marrow-mononuclear cells so as to induce vascularization in such diseased tissue.

21 Claims, 11 Drawing Sheets

THERAPEUTIC ANGIOGENESIS BY BONE MARROW-DERIVED CELL TRANSPLANTATION IN MYOCARDIAL ISCHEMIC TISSUE AND SKELETAL MUSCLE ISCHEMIC TISSUE

This application claims the benefit of copending U.S. Provisional Application No. 60/220,834, filed Jul. 26, 2000, the content of which is incorporated herein by reference in its entirety.

This invention is directed to methods of forming new blood vessels in diseased or damaged tissue such as ischemic tissue and increasing angiogenesis in diseased or damaged tissue by transplantation of autologous bone marrow-derived cells and uses of such methods to treat disease or injury wherein ischemic tissue is present and where angiogenesis is required.

BACKGROUND OF THE INVENTION

Neovascular formation in adults has been thought to result exclusively from proliferation, migration, and remodeling of preexisting endothelial cells (ECs), a process referred to as angiogenesis. (Folkman J. Nat Med. 1995; 1:27–30; Schaper W et al. Circ Res. 1971;28:671–679; Risau W. Nature, 1997,386:671–674) In contrast, vasculogenesis, a process defined as the formation of new blood vessels from endothelial progenitor cells (EPCs) during embryogenesis (Risau W. Nature 1997,386:671–674; Risau W. FASEB J. 1995;9:926–933; Risau W et al. et al. Development, 1988; 102:471–478), begins by the formation of blood islands that comprise EPCs and hematopoietic stem cells (HSCs). (Flamme I et al. Development 1992; 116:435–439; Hatzopoulos et al. Development. 1998;125:1457–1468) Blood islands fuse with each other to create primordial vascular networks in the embryo. EPCs and HSCs are believed to originate from common mesodermal ancestral cells (i.e., hemangioblasts) because of the presence of common cell surface antigens, such as Flk-1/KDR, Tie-2, and CD34. (Millauer B et al. Cell. 1993;72:835–846; Sato TN et al. Nature. 1995;376:70–74; Yano M et al. Blood. 1997;89:4317–4326; Krause DS et al. Blood. 1996;87:1–13)

Recently, circulating EPCs have been discovered in adult peripheral blood and human umbilical cord blood. (Asahara T et al. Science 1997;275:964–967; Murohara T et al. J. Clin Invest, 2000;105:1527–1536.) Circulating EPCs have been shown to participate in postnatal neovascularization after mobilization from bone marrow (BM). (Takahashi et al. Nat. Med. 1999; 5:434–438) Moreover, in an earlier study, Noishiki et al. raised the possibility of facilitating luminal endothelialization and mural angiogenesis in an artificial vascular prosthesis by BM transplantation. (Noishiki Y et al. Nat Med. 1996;2:90–93) Shi et al. recently showed that BM cells mobilized and participated in endothelialization of implanted artificial vascular grafts. (Shi Q et al. Blood. 1998;92:362–367) Although these studies suggest that EPCs originate from BM in adults, little is known as to whether functional EPCs can develop from adult BM cells and whether transplantation of autologous BM can quantitatively and functionally augment neovascular formation in ischemic tissues in adult species. These issues are relevant, because therapeutic angiogenesis is an emerging strategy to salvage tissues from critical ischemia. (Baumgartner I et al. Circulation. 1998; 97:1114–1123; Losordo DW et al. Circulation. 1998; 98:2800–2804; Isner J M and Asahara T J Clin Invest. 1999;103:1231–1236)

Accordingly, the studies of the present invention tested the hypotheses that (1) functional EPCs may develop from BM mononuclear cells (BM-MNCs) in adult animals and (2) transplantation of autologous BM-MNCs may augment neovascularization in response to tissue ischemia in a pig model of chronic myocardial ischemia and in a rabbit model of unilateral hindlimb ischemia.

Direct local transplantation of autologous BM-MNCs is a useful strategy for therapeutic neovascularization in ischemic tissues in adult mammals consistent with "therapeutic vasculogenesis."

SUMMARY OF THE INVENTION

This invention provides methods of forming new blood vessels in tissue in a subject, methods of increasing blood flow to tissue in a subject, and methods of increasing angiogenesis in tissue in a subject, which methods comprise: a) isolating autologous bone marrow-mononuclear cells from the subject; and b) transplanting locally into the tissue an effective amount of the autologous bone-marrow mononuclear cells, thereby forming new blood vessels in the tissue. The tissue may be ischemic tissue. The new blood vessels may be capillaries or collateral vessels in the ischemic tissue. Also provided are methods of treating tissue in disease or injury by local transplantation with an effective amount of the autologous bone marrow mononuclear cells so as to induce vascularization and repair in such diseased or damaged tissue. The treated tissue may be ischemic tissue.

This invention also provides a method of delivering a recombinant nucleic acid molecule to a diseased, damaged, ischemic or angiogenic site in a subject by transplantation at or near the site of disease, damage, ischemia or angiogenesis of an effective amount of the isolated autologous bone-marrow mononuclear cells from the subject, wherein the isolated bone-marrow mononuclear cells comprise a recombinant nucleic acid molecule encoding a protein of interest, i.e. a protein required or useful for tissue repair, perfusion, or angiogenesis.

BRIEF DESCRIPTION OF THE FIGURES

FIGS. 1g, 1h, and 1i are identical microscopic fields. Phase indicates phase-contrast microscopy.

FIGS. 2a and 2d, Phase-contrast (Phase) photomicrographs showing skeletal muscle fibers (M) in transverse section. Fluorescence microscopy (F1) of the same section revealed that fluorescence-labeled BM-MNCs (arrows) were incorporated into capillary-like EC networks among myocytes (FIG. 2b). No fluorescence-labeled BM-fibroblasts were detected, however (FIG. 2e). In the adjacent section (FIG. 2c), most fluorescence-positive BM-MNCs were costained with AP (arrows), indicating that transplanted cells had survived and participated in capillary structures. In contrast, there was spatial discrepancy between fluorescence-positive cells and AP-positive cells, indicating that transplanted BM fibroblasts were not incorporated into capillary structures. Sets 1a, 1b, 1c and 1d, 1e, 1f are the same microscopic fields, respectively. Representative photomicrographs from 8 (BM-MNC) and 5 (BM-fibroblast) animals are shown. Bars=50 µm.

FIG. 4b, Angiographic score at the ischemic hindlimb was significantly greater in the BM-MNC group than in the other 2 groups.

FIG. 5a, Representative photomicrographs of histological sections in ischemic skeletal muscles. Immunohistochemical staining for vWF and AP staining revealed the presence of numerous capillary ECs in a BM-MNC-transplanted animal. Fewer capillary ECs were observed, however, in control and fibroblast-transplanted animals. M indicates skeletal myocytes. Bars=50 µm. FIG. 5b, Quantitative analyses revealed that capillary density at ischemic skeletal muscle tissues (FIG. 5b, left) was significantly greater in the BM-MNC-transplanted group than in the other 2 groups. Capillary/muscle fiber ratio (FIG. 5b, right) was also greater in the BM-MNC group than in the other groups.

FIG. 6a, Representative LDPIs. Greater blood perfusion signals (red to white) in the ischemic thigh area were observed in a BM-MNC-transplanted rabbit, which contrasts with low perfusion signals (green to blue) in control and fibroblast-transplanted rabbits. FIG. 6b, Computer-assisted analyses of LDPIs revealed significantly greater blood perfusion values in the ischemic thigh area in the BM-MNC group than in the other 2 groups.

DETAILED DESCRIPTION OF THE INVENTION

Figures 1A, 1B, 1C, 1D, 1E, 1F, 1G, 1H, 1I:
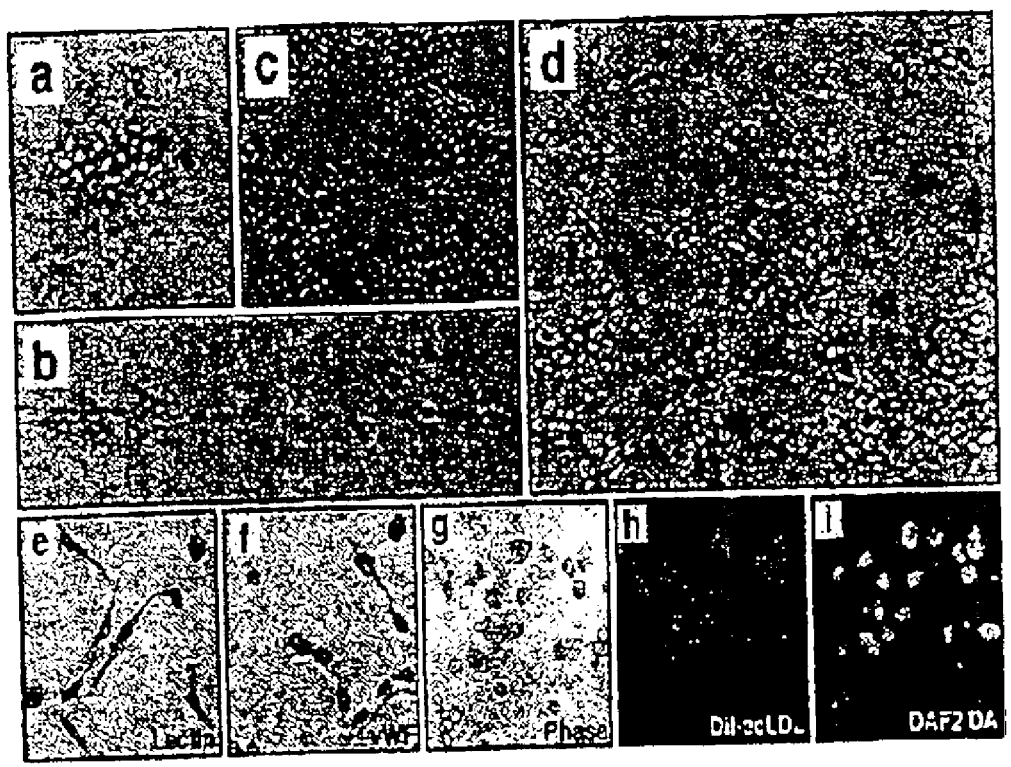
FIGS. 1a–1i. Differentiation of EPCs from rabbit BM-MNCs in vitro. Cell clusters appeared within 24 hours of culture of BM-MNCs (FIG. 1a). Spindle-shaped and AT cells appeared within 3 days of culture and formed linear cord-like structures (FIG. 1b) and multiple cell clusters. Cell clusters fused to form a larger cell monolayer (FIG. 1c) that turned into network structures (FIG. 1d). AT cells expressed EC-specific markers, such as Ulex lectin binding (FIG. 1e) and vWF (FIG. 1f). AT cells within cord-like structures (FIG. 1g) took up Dil-acLDL (FIG. 1h). AT cells also released NO, as assessed by DAF-2 DA (see Methods) (FIG. 1i).

The present invention is based in part on the following developments and discoveries: (1) a subset of BM-MNCs gives rise to EPCs in culture; (2) transplanted autologous BM-MNCs in an ischemic area can be incorporated into sites of neovascularization and arranged into the capillary network, whereas transplanted autologous BM-fibroblasts do not participate in the network formation; and (3) direct local transplantation of autologous BM-MNCs, but not of BM-fibroblasts, into ischemic tissue quantitatively and effectively augments neovascularization, collateral vessel formation, and blood flow in the ischemic tissue.

This invention provides a method of forming new blood vessels in tissue in a subject which comprises: a) isolating autologous bone marrow-mononuclear cells from the subject; and b) transplanting locally into the tissue an effective amount of the autologous bone-marrow mononuclear cells, thereby forming new blood vessels in the tissue. In a preferred embodiment of this method, the tissue is ischemic tissue. In another preferred embodiment of this method, the new blood vessels are capillaries. In a further preferred embodiment of the above-described method the new blood vessels are collateral blood vessels. In another embodiment, both capillaries and collateral blood vessels are formed. It is hypothesized that the transplanted bone-marrow mononuclear cells grow into, i.e. become, the new blood vessels This invention further provides a method of increasing blood flow to tissue in a subject which comprises: a) isolating autologous bone-marrow mononuclear cells from the subject; and b) transplanting locally into the tissue an effective amount of the autologous bone-marrow mononuclear cells so as to form new blood vessels in the tissue, thereby increasing the blood flow to the tissue in the subject. Preferably, the tissue is ischemic tissue or damaged tissue, wherein such tissue requires repair, regeneration or vasculogenesis. In a preferred embodiment of the methods described herein, the new blood vessels are capillaries. In another preferred embodiment the new blood vessels are collateral blood vessels. In a further embodiment, both capillaries and collateral blood vessels are formed.

This invention provides a method of treating diseased tissue in a subject which comprises: a) isolating autologous bone-marrow mononuclear cells from the subject; and b) transplanting locally into the diseased tissue an effective amount of the autologous bone-marrow mononuclear cells, thereby treating the diseased tissue in the subject. In a preferred embodiment the diseased tissue is ischemic tissue or tissue in need of repair or regeneration, as discussed infra.

This invention provides a method of increasing angiogenesis in diseased tissue in a subject which comprises: a) isolating autologous bone-marrow mononuclear cells from the subject; and b) transplanting locally into the diseased tissue an effective amount of the autologous bone-marrow mononuclear cells, thereby increasing angiogenesis and repair in the diseased tissue in the subject. In a preferred embodiment the tissue is ischemic tissue or tissue in need of repair or regeneration.

This invention also provides a method of preventing heart failure in a subject which comprises: a) isolating autologous bone-marrow mononuclear cells from the subject; and b) transplanting locally into heart tissue an effective amount of the autologous bone-marrow mononuclear cells so as to result in formation of new blood vessels in the heart tissue, to increase angiogenesis and repair in the heart tissue in the subject, thereby preventing heart failure in the subject. In a preferred embodiment the heart tissue is ischemic heart tissue or heart tissue in need of repair or regeneration after injury or surgery. In other preferred embodiments, compromised or occluded coronary blood vessels are treated by the above-described methods resulting in formation of new blood vessels.

This invention provides a method of regenerating tissue in a subject which comprises: a) isolating autologous bone-marrow mononuclear cells from the subject; and b) transplanting locally into the tissue an effective amount of the autologous bone-marrow mononuclear cells, resulting in formation of new blood vessels in the tissue, i.e. increasing angiogenesis and repair in diseased tissue in the subject. In a preferred embodiment the tissue is diseased tissue. More preferably, the diseased tissue is ischemic tissue or damaged tissue in need of repair or regeneration.

In the methods of the subject invention, autologous bone-marrow is isolated from the subject usually under general anesthesia by aspiration from the tibia, femur, ilium or sternum with a syringe, preferably containing 1 mL heparin with an 18-gauge needle. Bone-marrow mononuclear cells are isolated using standard techniques with which one of skill is familiar; such techniques may be modified depending upon the species of the subject from which the cells are isolated. The marrow cells are transferred to a sterile tube and mixed with an appropriate amount of medium, e.g., 10 mL culture medium (Iscove's modified Dulbecco medium IMDM with 10% fetal bovine serum, penicillin G [100 U/mL] and streptomycin [100 µg/mL]). The tube is centrifuged to pellet the bone marrow cells, e.g., at 2000 rpm for five minutes and the cell pellet resuspended in medium, e.g., 5 mL culture medium. Low density bone-marrow mononuclear cells are separated from the suspension, e.g., by density gradient centrifugation over Histopaque-1083™ (Sigma), e.g. as described by Yablonka-Reuveni and Nameroff and hereby incorporated by reference. (Histochemistry (1987) 87:27–38). Briefly, the cell suspension is loaded on 20% to 60% gradient, e.g. Histopaque-1083™(Sigma), Ficoll-Hypaque or Percoll (both available from Pharmacia, Uppsala, Sweden) according to manufacturer's instructions and as described by Yablonka-Reuveni and Nameroff. For example, the cells are centrifuged at 400 g for 20 minutes for Ficoll-Hypaque or at 2000 rpm for 10 minutes for Percoll. Following centrifugation, the top two-thirds of total volume are transferred into a tube, as these layers contain most of the low density bone-marrow mononuclear cells. The cells are centrifuged, e.g. at 2000 rpm for 10 minutes to remove the Histopaque. This is repeated and the cell pellet of bone-marrow mononuclear cells is resuspended in culture medium or buffer, e.g., IMM, saline, phosphate buffered saline, for transplantation. Preferably, fresh bone-marrow mononuclear cell, isolated as described above, are used for transplantation.

The bone-marrow mononuclear cells may also be cultured in any complete medium containing up to 10% serum, e.g., IMDM containing 10% fetal bovine serum and antibiotics, as described above, for up to four weeks before transplantation. The cells may be cultured with growth factors, e.g., vascular endothelial growth factor. The medium is changed about twice a week. The cultured cells are dissociated from the culture dishes with 0.05% trypsin (Gibco BRL, Grand Island, N.Y.), neutralized with culture medium and collected by centrifugation, for example, at 2000 rpm for five minutes at room temperature. The cells are resuspended in IMDM at a concentration of $\approx 1\times 10^5$ cells to about $1\times 10^{10}$ cells, preferably about $1\times 10^7$ cells to about $1\times 10^8$ cells in 50 µL for transplantation.

The autologous bone-marrow mononuclear cells are transplanted by injection into the center, bordering zone, or neighboring areas of the ischemic tissue. In additional embodiments of the present invention, the autologous bone-marrow mononuclear cells may be transplanted into or near any site of any tissue in which angiogenesis or repair is required. Such tissue includes but is not limited to underperfused tissue of any end-organ, e.g. tissues with chronic ischemia. Such underperfused tissue includes but is not limited to the heart, brain, skeletal muscle, kidney, liver, organs of the gastrointestinal tract and other organs and tissues requiring repair.

The transplanted autologous bone-marrow mononuclear cells are delivered to the desired tissue site(s) in an effective amount of $\approx 1\times 10^5$ cells to about $1\times 10^{10}$ cells, preferably about $1\times 10^7$ cells to about $1\times 10^8$ cells, per injection site, preferably by needle injection. Preferably, a tissue receives a total of about fifty injections, e.g. for a leg or arm, and about ten injections into heart muscle. Alternatively, the autologous bone-marrow mononuclear cells are delivered by intravascular injection or infusion into arteries or veins, endoluminal injection directly into an occlusion, retrograde perfusion, pericardial delivery, implants (biodegradable or biostable), e.g. local implant scaffold, patch, needle-free injection using propulsion by gas such as $CO_2$, acceleration or transfer into tissue by other means such as iontophoresis or electroporation, pressure or application to a tissue or organ surface. In general, delivery may be accomplished with the use of any medical device for delivery of transplanted cells.

In preferred embodiments of any of the methods described herein, the tissue into which autologous bone-marrow mononuclear cells are transplanted includes any diseased or damaged tissue and any tissue in need of repair or regeneration, including but not limited to underperfised tissue such as tissue found in chronic ischemia. Preferably, the tissue includes but is not limited to ischemic tissue. More preferably the tissue includes such tissue as cardiac muscle tissue, skeletal muscle tissue, brain tissue e.g., affected by stroke or AV malformations, coronary vessels, kidney, liver, organs of the gastrointestinal tract, muscle tissue afflicted by atrophy, including neurologically based muscle atrophy. In further embodiments the subject is preferably a mammal. Most preferably, the mammal is a human.

Prior studies have suggested that EPCs, mature ECs, and HSCs share cell surface antigens, such as CD34, Flk-1/KDR, and Tie-2, in humans (Millauer B et al. *Cell.* 1993;72:835–846; Sato TN et al. *Nature.* 1995;376:70–74; Yano M et al. *Blood.* 1997;89:4317–4326; Krause DS et al. *Blood.* 1996;87:1–13). CD34 and KDR have been used as landmark molecules to isolate human EPCs (Asahara T et al. *Science* 1997;275:964–967; Murohara T et al. *J. Clin Invest,* 2000;105:1527–1536.) The ideal would be to be able to isolate purified EPCs from BM-MNCs for use in transplantation (Murohara T et al. 2000 supra; Kalka C et al. *Proc*

*Natl Acad Sci USA*. 2000;97:3422–3427). However, in the rabbit studies undertaken herein no specific antibodies for rabbit CD34 or rabbit EPCs were available. Nevertheless, the in vitro study disclosed herein showed that EPCs did develop from rabbit BM-MNCs. During culture on fibronectin, a subpopulation of rabbit BM-MNCs gave rise to spindle shaped AT cells that had many characteristic functions and markers for endiothelial lineage, such as acLDL uptake, NO release, and positive immunostainings for vWF and ulex lectin binding. Moreover, AT cells formed linear cord-like as well as network structures (FIG. 1), which were similar to those created by human EPCs in previous studies. (Asahara T et al. 1997 supra and Murohara T et al. 2000 supra) Therefore, AT cells have now been defined as a major population of EPCs in the present study. Thus it is not essential that EPCs be purified for use in the present invention. Isolation of BM-MNCs and transplantation thereof provides the desired beneficial effect. Moreover, use of BM-MNCs in the methods of the present invention provides increased blood vessel development at the site of the transplantation.

It has been reported that coculture of human CD34+and CD34 MNCs yielded a greater number of EPCs than culture of CD34+MNCs alone, suggesting that intercellular communication between CD34+MNCs and the remaining CD34-cells is important for the differentiation of EPCs. (Asahara T et al. 1997 supra and Murohara T et al. 2000 supra) Thus, it was thought that BM-MNCs without purification of EPCs might be a sufficient and even more effective cellular source for therapeutic neovascularization. Transplantation of BM-MNCs consistently augmented angiogenesis and collateral vessel formation in the ischemic tissue in the present study. These effects do not appear to be due to a nonspecific action of cell transplantation, because transplantation of BM-fibroblasts fails to augment angiogenesis or tissue repair.

There may be additional mechanisms for the accelerated angiogenesis induced by transplanted BM-MNCs. BM contains nonhematopoietic stromal cells, which comprise immature mesenchymal stem cells, EPCs, fibroblasts, osteoblasts, ECs, and adipocytes, and these cells can proliferate and may act as feeder cells for EPCs. (Prockop D J *Science*. 1997;276:71–74) Cell transplantation that included such feeder cells was used effectively to accelerate skin healing in animals, a process dependent on angiogenesis. (Bell E, Ehrlich H P, Buttle D J, et al. Living tissue formed in vitro and accepted as skin-equivalent tissue of full thickness. *Science*. 1981;211:1052–1054) In the study herein, 49% of the isolated BM-MNCs were either monocytoid or lymphocytoid cell fractions, in which BM stromal cells, including EPCs, are believed to be present. (Asahara T et al. *EMBO J*. 1999;18:3964–3972) Moreover, BM-MNCs are likely to contain HSCs, which were recently shown to be proangiogenic by releasing angiopoietin-1, a ligand for Tie-2. (Takakura N et al. *Cell*. 2000;102:199–209) Taken together, when BM-MNCs are transplanted in the methods of the present invention, a mixture of different kinds of cells work cooperatively with each other as feeder cells, and a greater number of EPCs develop after in vivo BM transplantation.

In the present invention, autologous BM-MNCs were locally transplanted into ischemic tissues. There are several advantages of local transplantation rather than 15 intravenous transfusion of BM-MNCs for therapeutic neovascularization. First, through local transplantation, one can increase the density of EPCs at the target tissue compared with intravenous infusion. In the present invention, $\approx 1 \times 10^5$ cells to about $1 \times 10^{10}$ cells, preferably about $1 \times 10^7$ cells to about $1 \times 10^8$ cells per injection site are delivered, preferably by needle injection within or near the diseased or damaged tissue or any tissue in need of repair or tissue regeneration, e.g. ischemic tissues. This may be an advantage for cell survival in the tissues, because it is believed that cells must form clusters to survive in tissues. In cancer cells, for example, there must be a clump of $\geq 50$tumor cells to form a new metastasis colony in remote tissues. Second, local transplantation may reduce the systemic side effects of transplanted BM-MNCs compared with systemic infusion. Systemic intravenous administration of BM-MNCs or EPCs may potentially elicit adverse effects on angiogenic disorders such as cancers, rheumatoid arthritis, and diabetic retinopathy.

Other preferred means of delivery of autologous BM-MNCs to the tissue include but are not limited to delivery by intravascular injection or infusion into arteries or veins, endoluminal injection directly into an occlusion, retrograde perfusion, pericardial delivery, implants (biodegradable or biostable), e.g. local implant scaffold, patch, needle-free injection using propulsion by gas such as $CO_2$, acceleration or transfer into tissue by other means such as iontophoresis or electroporation, pressure or application to a tissue or organ surface. In general, delivery may be accomplished with the use of any medical device for delivery of transplanted cells. Preferably each tissue receives a total of about ten to fifty injections.

In the present invention autologous BM-MNCs are transplanted to an ischemic tissue where they become incorporated into or participate in the formation of new blood vessels and/or capillaries. According to the methods of the present invention, autologous rabbit BM-MNCs ($1 \times 10^6$ cells) were labeled with a green fluorescent marker and locally transplanted into the ischemic limb. Examination under fluorescence microscopy 14 days after transplantation revealed that the labeled BM-MNCs changed their shape to a spindle form and were sprouting from the sites of injection and incorporated into the capillary networks among the skeletal myocytes (FIG. 2). Importantly, the fluorescence-positive (transplanted) cells were costained with AP in adjacent sections. Because the method of AP detection used relies on the intrinsic enzyme activity within ECs, positive AP staining confirmed that the transplanted BM-MNCs survived in the ischemic tissues. (Ziada AM et al. *Cardiovasc Res*. 1984;18:724–732) In contrast, transplanted fluorescence-labeled autologous BM fibroblasts did not participate in capillary-like structures, indicating the specific nature of BM-MNCs for neovascularization.

BM transplantation is currently used for the treatment of a variety of neoplastic diseases after chemotherapy. A significant obstacle limiting the efficacy of allogenic BM transplantation, however, is the occurrence of graft-versus-host diseases. (Bortin MM et al. *Ann Intern Med*. 1992;116:505–509) In this sense, one of the greatest advantages of the present invention is the use of autologous BM-MNCs for therapeutic neovascularization in adults, which eliminates graft-versus-host diseases. Moreover, the amount of autologous BM blood used for therapeutic neovascularization was 3 to 4 mL per animal (ie, 0.1% of body weight) in the present study. Aspiration of such an amount or more (up to 800 ml) of BM from a human subject is performed safely, and thus, the protocol provided by the present invention is also feasible for patients with peripheral arterial occlusive disease.

In summary, the present invention provides a subset of adult BM-MNCs that differentiates into EPCs, which acquire EC phenotypes in vitro. Transplanted autologous BM-MNCs survive and are successfully incorporated into the capillary EC network among skeletal myocytes at sites of active angiogenesis and repair in vivo. Finally, transplantation of BM-MNCs quantitatively augments neovascularization and collateral vessel formation in the ischemic tissues. The present invention therefore has several important clinical implications. First, autologous transplantation of BM-MNCs represents a new strategy for clinical application designed to revascularize and repair ischemic tissues and other types of damaged or diseased tissues. Second, the fact that transplanted BM-MNCs participate in active angiogenesis in adult tissues provides an additional utility of BM-MNCs as vectors for gene delivery to damaged tissue sites or diseased tissue sites in vivo.

In a further aspect of the present invention, BM-MNCs may be used as vectors for gene delivery to ischemic and/or angiogenic sites in vivo. Accordingly, there is provided a method of delivering a recombinant nucleic acid molecule to a diseased tissue site in a subject which comprises: a) isolating autologous bone-marrow mononuclear cells from the subject; b) inserting into the isolated autologous bone-marrow mononuclear cells the recombinant nucleic acid molecule to form transformed bone-marrow mononuclear cells; and c) administering to the diseased tissue site an effective amount of the transformed bone marrow mononuclear cells. In a preferred embodiment, the diseased tissue site is ischemic tissue, e.g. cardiac or skeletal ischemic tissue, or other tissue in need of repair, regeneration or angiogenes is, as discussed below.

In another aspect of this invention, provided is a method of delivering a recombinant nucleic acid molecule to an angiogenic site or damaged tissue site in a subject which comprises: a) isolating autologous bone-marrow mononuclear cells from the subject; b) inserting into the isolated autologous bone-marrow mononuclear cells the recombinant nucleic acid molecule to form transformed bone-marrow mononuclear cells; and c) administering to the angiogenic site or damaged tissue site an effective amount of the transformed bone marrow mononuclear cells.

The recombinant nucleic acid molecule to be inserted in the BM-MNCs will depend upon the type of gene therapy desired for treatment of a particular disease. Methods of introducing genes into a human subject by gene therapy, i.e. introducing into a human subject human cells which have been transformed with human genes are known. Such methods have been described in Andersen et al., U.S. Pat. No. 5,399,346, and are incorporated herein by reference.

Recombinant genes useful in the methods of the present invention include known nucleic acid molecules which encode a protein of interest, such protein being useful in the treatment of the subject. In preferred embodiments the nucleic acid molecule encodes proteins such as growth factors, including but not limited to, VEGF-A, VEGF-C PlGF, KDR, EGF, HGF, FGF, angiopoietin-1, and cytokines. In additional preferred embodiments, the nucleic acid molecule encodes endothelial nitric oxide synthases eNOS and iNOS, G-CSF, GM-CSF, VEGF, aFGF, SCF (c-kit ligand), bFGF, TNF, heme oxygenase, AKT (serine-threonine kinase), HIFα(hypoxia inducible factor), Del-1 (developmental embryonic locus-1), NOS (nitric oxide synthase), BMP's (bone morphogenic proteins), SERCA2a (sarcoplasmic reticulum calcium ATPase), $\beta_2$-adrenergic receptor, SDF-1, MCP-1, other chemokines, interleukins and combinations thereof In additional preferred embodiments, genes which may be delivered in the autologous BM-MNCs using the methods of the present invention include but are not limited to nucleic acid molecules encoding factor VIII/von Willebrand, factor IX and insulin, NO creating genes such as eNOS and iNOS, plaque fighting genes thrombus deterrent genes, for example.

Known nucleic acid sequences which may be used in the methods of the present invention include but not limited to the DNA sequences of KDR (Terman et al., U.S. Pat. No. 5,861,301), EGF (Ullrich et al. Nature, 309:418–425 (1986)), G-CSF (Nagata et al. EMBO J. 5:575 (1986)), GM-CSF (Wong et al. Science 22:810 (1985)), M-CSF (Welte et al. PNAS USA 82:1526 (1985), TNF (Porter, TiBTech 9:158(1991), TNF-α(Beutler et al. Nature 320:584 (1986)), TNF-β(Gray et al. Nature 312:721(1984)),IL-2 (Feitscher et al. Lymphok. Res. 6:45(1987));IL-4(Lee et al. PNAS USA 83:2061(1986)), are hereby incorporated by reference.

The recombinant nucleic acid molecule(s) encoding the desired protein(s) may be produced by polymerase chain reaction from known DNA sequences as described by Saiki et al. Science 239:487–491 (1988) and Mullis et al., U.S. Pat. No. 4,683,19, which is incorporated herein by reference. Alternatively, DNA may be chemically synthesized as described by Caruthers Science 230(47223): 281–285 (1985), which is incorporated herein by reference, using commercially available equipment.

Briefly, RNA is isolated and purified from a suitable cell/tissue source of the desired nucleic acid and cDNA is synthesized by standard procedures as described in Sambrook et al. Molecular Cloning—A Laboratory Handbook, Cold Spring Harbor Laboratory Press (1989) and in Ausubel et al. (Eds.) Current Protocols in Molecular Biology, Greene Associates/Wiley Interscience, New York (1990). The desired DNA sequence may be replicated by inserting such sequence into any of the many available DNA cloning vectors using known techniques of recombinant DNA technology. The cloning vector may be a plasmid, phage or other DNA sequence which is able to replicate autonomously in a host cell; such a vector has at least one endonuclease recognition site at which such DNA sequence may be cut without loss of essential biological function of the vector. Suitable cloning vectors include prokaryotic cloning vectors such as plasmids from E. coli, e.g. colE1, pCR1, pBR322, pMB9, pUC, PKSM, and RP4; derivatives of phage DNA, e.g. M13 and other filamentous single-stranded DNA phages. The desired DNA sequence is spliced into the cloning vector for replication and cloning. The vector may contain a marker, such as tetracycline resistance or ampicillin resistance to facilitate identification of cells transformed with said vector.

A full length clone of the recombinant nucleic acid molecule encoding the proteins of interest, i.e., preferably those having the entire coding region of the desired protein, is inserted into a suitable expression vector for delivery into BM-MNCs. The cloned gene is operably linked in the vector, i.e. placed under the control of, at least one regulatory element required for expression, i.e. a promoter sequence which may also contain enhancer sequences, termination sequences, splice signals, tissue-specific elements, and/or translation initiation and termination sites. Useful expression control sequences include but are not limited to, the lac promoter system, the trp system, the tac system, the trc system, major operator and promoter regions of phage lambda.

Gene delivery may be either endogenously or exogenously controlled. Examples of endogenous control include promoters which are sensitive to a physiological signal such as hypoxia or glucose elevation. Exogenous control systems involve gene expression controlled by administering a small molecule drug. Examples include tetracycline, doxycycline, ecdysone and its analogs, RU486, chemical dimerizers such as rapamycin and its analogs, etc.

Vectors for use in mammalian cells include derivatives of SV-40, adenovirus, retrovirus-derived DNA sequences and shuttle vectors derived from combinations of functional mammalian vectors and functional plasmids and phage DNA. Eukaryotic expression vectors are well known, e.g. such as those described by P J Southern and P Berg, *J Mol Appl Genet* 1:327–341 (1982); Subramini et al., *Mol Cell. Biol.* 1:854–864 (1981), Kaufinann and Sharp, *J Mol. Biol.* 159:601–621 (1982); Scahill et al., *PNAS USA* 80:4654–4659 (1983) and Urlaub and Chasin *PNAS USA* 77:4216–4220 (1980), which are hereby incorporated by reference. The vector used in the methods of the present invention may be a viral vector, preferably a retroviral vector. Replication deficient adenoviruses are preferrred. For example, a "single gene vector" in which the structural genes of a retrovirus are replaced by a single gene of interest, under the control of the viral regulatory sequences contained in the long terminal repeat, may be used, e.g. Moloney murine leukemia virus (MoMulV), the Harvey murine sarcoma virus (HaMuSV), murine mammary tumor virus (MuMTV) and the murine myeloproliferative sarcoma virus (MuMPSV), and avian retroviruses such as reticuloendotheliosis virus (Rev) and Rous Sarcoma Virus (RSV), as described by Eglitis and Andersen, BioTechniques 6(7):608–614 (1988), which is hereby incorporated by reference.

Recombinant retroviral vectors into which multiple genes may be introduced may also be used according to the methods of the present invention. As described by Eglitis and Andersen, supra, vectors with internal promoters containing a cDNA under the regulation of an independent promoter, e.g. SAX vector derived from N2 vector with a selectable marker (noe$^R$) into which the cDNA for human adenosine deaminase (hADA) has been inserted with its own regulatory sequences, the early promoter from SV40 virus (SV40) may be designed and used in accordance with the methods of the present invention by methods known in the art.

The vectors comprising the recombinant nucleic acid molecule are incorporated, i.e. infected, into the BM-MNCs by plating $\approx 5 \times 10^5$ BM-MNCs over vector-producing cells for 18–24 hours, as described by Eglitis and Andersen BioTechniques 6(7):608–614 (1988), which is hereby incorporated by reference.

DNA encoding the desired protein(s) may also be inserted into BM-MNCs by electroporation, ultrasound, chemical methods, such as calcium phosphate mediated transfection, encapsulation of DNA in lipid vesicles, or physical means such as microinjection, as described by Eglitis and Andersen BioTechniques 6(7):608–614 (1988), which is hereby incorporated by reference.

The BM-MNCs comprising the recombinant nucleic acid molecule (either infected with the vector containing the recombinant nucleic acid molecule of interest or transfected with the DNA) are transplanted locally by delivery to a subject into or near a tissue site in need of repair, regeneration, angiogenesis and/or gene therapy, e.g. an ischemic site or damaged or diseased tissue, by needle injection. Preferably, $\approx 1 \times 10^5$ vector infected-BM-MN cells to about $1 \times 10^{10}$ vector-infected BM-MN cells are injected per injection site. More preferably, about $1 \times 10^7$ vector infected-BM-MN cells to about $1 \times 10^8$ vector infected-BM-MN are delivered to the ischemic, damaged or angiogenic site. Other preferred means of delivery of autologous BM-MNCs to the tissue include but are not limited to delivery by intravascular injection or infusion into arteries or veins, endoluminal injection directly into an occlusion, retrograde perfusion, pericardial delivery, implants (biodegradable or biostable), e.g. local implant scaffold, patch, needle-free injection using propulsion by gas such as $CO_2$, acceleration or transfer into tissue by other means such as iontophoresis or electroporation, pressure or application to a tissue or organ surface. In general, delivery may be accomplished with the use of any medical device for delivery of transplanted cells. Preferably each tissue receives a total of about ten to fifty injections.

Preferably, the ischemic, damaged or diseased tissue and/or angiogenic site includes but is not limited to cardiac muscle tissue, skeletal muscle tissue, a compromised or occluded coronary blood vessel, a compromised or occluded peripheral blood vessel, any natural diseased tissue site or injury site in the subject which requires new or additional blood vessels, including but not limited to the brain, kidney, liver, organs of the gastrointestinal tract, an atrophied muscle, skin and lung. The ischemic or angiogenic site may also be an artificially created site. Preferably, diseases which may be treated by injection of the autologous BM-MNCs into which the nucleic acid molecules of interest have been incorporated include but are not limited to diabetes, vascular ulcers, vascular wounds or other tissue wounds, hemophilia, Reynaud's phenomena, pressure sore, burn, moyamoya disease, bone fracture, chronic renal failure (with anemia), chronic hepatitis, or other microcirculatory disorders, vasospastic angina, heart failure, stroke, AV malformations, Parkinson's disease, epilepsy, Alzheimer's disease, Huntington's disease, liver failure, muscular dystrophy, cancer, infections resulting in tissue damage such as myocarditis. In preferred embodiments, the tissues which may be treated by local autologous BM-MNC transplantation include damaged tissue wherein the damage is caused by any disease which results in cell death, i.e. apoptosis or tissue necrosis, or wherein the damage is a result of aging, injury or surgery, such tissue requiring repair and/or regeneration. In further embodiments the subject is preferably a mammal. Most preferably, the mammal is a human.

The invention will be better understood from the examples which follow, however the invention is not limited to these examples, which are solely intended to be illustrative thereof

EXAMPLE 1

Augmentation of Postnatal Neovascularization With Autologous Bone Marrow Transplantation
Isolation of Rabbit BM-MNCs All animal protocols were approved by the Institutional Animal Care and Use Committee of Kurume University. Animals were anesthesized with ketamine 50 mg/kg and xylazine 5 mg/kg and BM (3 to 5 mL) was aspirated from the right iliac crest. BM-MNCs were then isolated by centrifugation through a Ficoll Histopaque™ density gradient as described previously. (Murohara et al. *J Clin Invest.* 2000; 105:1527–1536)

BM-MNCs were isolated from rabbit BM blood using the Histopaque-density centrifugation method. As discussed below, the medium used for cell culture experiments was Medium 199 supplemented with 20% FBS, bovine pituitary extract as an EC growth supplement, heparin (100 µg/mL) and antibiotics (Life Technologies, Grand Island, N.Y.) (standard medium). MNCs were cultured on human fibronectincoated plastic plates (BIOCOAT, Becton-Dickson).

Briefly, as described by Yablonka-Reuveni and Nameroff the cell suspension is loaded on a 20% to 60% density gradient. The cells are centrifuged at 14000 rpm for 10 minutes. The top two thirds are transferred into a tube. The cells are centrifuged at 2000 rpm for 10 minutes and then washed with PBS to remove the Percoll. This is repeated and the cell pellet suspended in culture medium (IMBM) as described above. The freshly isolated BM-MNCs may be transplanted or the cells may be plated on plastic tissue culture dishes for one hour to avoid contamination by differentiated adhesive cells. Alternatively, the BM-MNCs may be cultured up to four weeks before transplanataion, as described above.

BM-MNCs were shown to contain erythroblasts (37±6%), monocytoid cells (12±2%), lymphocytoid cells (37±10%), and granulocytes (14±2%) by May-Giemsa staining (n=4). BM stromal cells, including EPCs, are believed to be present in monocytoid and/or lymphocytoid cell fractions. (Prockop D J, *Science* 1997; 276:715–74; Asahara T et al. *EMBO J* 1999;18:3964–3972)

Cell Culture

BM-MNCs were cultured on fibronectin-coated plates in Medium 199 (Gibco BRL, Life Technologies, Gibco Catalog No. 11150–059) with 20% FBS, endothelial cell growth supplement, heparin 10 U/mL, and antibiotics [Penicillin G+Streptomycin+Amphotericin B] (Gibco Catalog No. 15240–062) (standard medium), at 37° C. under 5% $CO_2$. Cultures were examined for the development of cell clusters and cord-like structures, typical morphological appearances or EPCs, as described previously and incorporated herein by reference (Asahara T et al. *Science.* 1997;275:964–967; Murohara T et al. *J. Clin Invest*, 2000;105:1527–1536.) At day seven of culture, EC-specific functions and markers were evaluated as described below.

Rabbit BM-derived fibroblasts devoid of HSCs were isolated and cultured from attached BM stromal cells after a series of passages. Fibroblasts were subcloned by limiting dilution and cultured in standard medium. Fibroblasts were identified by their typical "hairwave"-like morphology. Negative von Willebrand factor (vWF) expression and DiI-acetylated LDL (DiI-acLDL, i.e. 1,1'-dioctadecyl-3,3,3',3'-tetramethylindocarbocyanine perchlorate-labeled acetylated low-density lipoprotein) incorporation indicated that there was no contamination of ECs or EPCs.

Immunocytochemistry for EPCs

Immunocytochemical analysis was performed to identify the expression of vWF and Ulex europaeus lectin (Sigma) binding as markers of EC lineage as described previously by Murohara et al. (*J Clin Invest* 2000; 105:1527–1536) and Jackson et al. (*J Cell Sci* 1990; 96:257–262) Briefly, spindle-shaped and AT cells at day seven of culture are grown on chamber slides and fixed with cold methanol. Endogenous peroxidase is inactivated with 3% hydrogen peroxide. Non-specific monoclonal antibody binding is blocked with 10% horse serum. Primary monoclonal antibodies against human vWF (clone F8/86; DAKO, Glostrup, Denmark) are then applied. The monoclonal antibodies are mouse $IgG_1$ and thus negative control slides are incubated with appropriate dilution of MOPC-21 (Sigma), a nonimmune mouse $IgG_1$. After two washes with PBS, a biotinylated horse anti-mouse $IgG_1$ is applied, which is followed by the avidin-biotin immunoperoxidase treatment (Vector Laboratories, Burlingame, Calif., USA). Any secondary antibody can be used as long as it is an anti-mouse IgG, e.g. rabbit or goat anti-mouse IgG. To visualize the final immunoreaction products, 3-amino-9-ethylcarbazole (Histofine; Nichirei, Tokyo, Japan) is used.

Functional Studies for EPCs in Culture

An analysis of whether EPCs incorporated acLDL, one of the characteristic functions of ECs, was performed as described previously by Murohara et al. *J Clin Invest* 2000; 1051527–1536 using the method of Voyta et al. *J Cell Biol* 1984; 99:2034–20401984 which are hereby incorporated by reference Briefly, attaching cells (AT) are cultured on fibronectin in medium containing 15 μg/mL DiI-labeled Ac-LDL (DiI-Ac-LDL; Molecular Probes, Eugene, Oreg. USA) for 24 hours at 37° C. Cells are then examined under a fluorescence microscope to determine DiI-Ac-LDL.

Release of NO from EPCs was also analyzed using a membrane permeable NO detection reagent, diaminofluorescein-2-diacetate (DAF-2 DA, Daiichi Chemicals) as described previously by Kojima et al. which is hereby incorporated by reference (*Anal Chem.* 1998;70:2446–2453). When DAF-2 DA reacts with free NO, the compound yields the green-fluorescent triazole (lower detection limit of NO is 5 nM). Briefly, cells, which have been washed twice with Ca2+-free PBS are then bathed in Krebs-Henseleit buffer containing L-arginine (1 mM) and 10 μM DAF-2 DA and incubated for one hour at 37° C. NO formation in the cells, as detected by nitrosylated DAF-2 DA, is examined under a fluorescence microscope.

Rabbit Model of Unilateral Hindlimb Ischemia

Neovascular formation in response to tissue ischemia was examined in a rabbit model of unilateral limb ischernia, as described in Murohara et al. which is hereby incorporated by reference (Murohara et al. *J Clin Invest* 1998; 101:2967–2978). Briefly, Male New Zealand White rabbits (2.6 to 3.6 kg) (Pine Acre Rabbitry, Norton Ma) were anesthetized with xylazine (2 mg/kg), followed by ketamine (50 mg/kg) and acepromazine (0.8 mg/kg). After the skin incision, the entire femoral artery and all of its major branches were dissected free. The external iliac artery and all of the abovementioned arteries were ligated with 4–0 silk (Ethicon, Sommerville, N.J.). Finally, the femoral artery was excised from its proximal origin as a branch of the external iliac artery to the point distally where it bifurcates into the saphenous and popliteal arteries. As a consequence, blood flow to the ischemic limb becomes completely dependent upon collateral vessels issuing from the internal iliac artery.

Detection of Transplanted BM-MNCs or BM-Fibroblasts in Ischemic Tissues

An analysis of whether transplanted autologous BM-MNCs or BM-fibroblasts survive and participate in the formation of capillary structures in the ischemic tissues was undertaken. Rabbits were subjected to unilateral limb ischemia as described above. At day seven, autologous BM-MNCs (n=8) or BM-fibroblasts (n=5) were labeled with a green fluorescent marker, PKH2-GL (Sigma) as described previously and incorporated herein by reference (Yuan Y and Fleming B P *Microvasc Res.* 1990;40:218–229; Murohara. T et al. *J Immunol.* 1996;156:3550–3557). Labeled BM-MNCs or BM-fibroblasts ($5\times10^6$ cells per animal) were then transplanted into the ischemic thigh skeletal muscles with a 26-gauge needle at six different points. At day 21 (14 days after transplantation), rabbits were euthanized with an overdose of pentobarbital, and four pieces of ischemic tissue per animal were obtained. Multiple frozen sections five μm thick were prepared and were examined under fluorescence microscopy.

To examine whether transplanted BM-MNCs or BM-fibroblasts survived in the tissues, adjacent frozen sections were subjected to alkaline phosphatase (AP) staining for one hour at 37 to 38° C., by an indoxyl-tetrazolium method as described previously and incorporated herein by reference (Takeshita et al. *J Clin Invest.* 1994; 93:662–670; Ziada AM et al. *Cardiovasc Res.* 1984;18:724–732). AP staining can detect capillary ECs in the skeletal muscle tissues as well. The AP staining turns capillary ECs dark blue only when ECs are viable and the intracellular enzyme activity remains intact. The spatial relationship between fluorescence-positive cells and AP-positive cells was examined to determine whether transplanted cells (BM-MNCs or BM-fibroblasts) participated in the formation of capillary structures.

Therapeutic Neovascularization by BM Transplantation

Additional rabbits (n=27) were subjected to unilateral limb ischemia and were randomly divided into three groups. No rabbit died during the experimentation. The control group (n=8) received 2.5 mL saline. The second group (n=13) received autologous BM-MNCs ($6.9 \pm 2.2 \times 10^6$ cells per animal; BM-MNC group), and the third group (n=6) received autologous BM-fibroblasts ($6.5 \pm 1.5 \times 10^6$ cells per animal; BM-fibroblast group) transplanted into the ischemic muscles at postoperative day seven. In brief, either autologous BM-MNCs or BM-fibroblasts were isolated and suspended in 2.5 mL of saline. Within ten minutes after cell preparation, cells were transplanted at 6 different points in the ischemic thigh skeletal muscles. After transplantation of BM-MNCs or BM-fibroblasts or saline injection, angiogenesis and collateral vessel formation in the ischemic limb tissues were analyzed as described below.

Calf Blood Pressure Ratio

Systolic calf blood pressure (CBF) in both hindlimbs was measured with a cuff blood pressure monitor system (Johnson & Johnson) before surgery, at day seven (before cell transplantation), and at day 35. On each occasion, measurement was performed in triplicate and the mean value was calculated. The CBP ratio was defined as the ratio of the ischemic/normal limb CBP and is considered a useful physiological parameter representing the extent of collateral blood flow, as described previously and incorporated by reference (Takeshita et al. *J Clin Invest.* 1994; 93:662–670; Murohara et al. *J Clin Invest.* 1998;101:2967–2578).

Angiography

Formation of collateral vessels was evaluated by angiography at postoperative day 35. A 5F catheter was inserted through the right common carotid artery and advanced to the lower abdominal aorta. Angiography was performed with an x-ray angiography system (OEC Medical). Angiographs were taken at four seconds after the injection of nonionic contrast medium (Schering). To quantitatively assess the extent of collateral vessel formation, the angiographic score was calculated as described previously (Takeshita et al. *J Clin Invest.* 1994; 93:662–670). Briefly, a composite of 5-mm$^2$ grids was placed over the medial thigh area of the four seconds (4-s) angiogram. The total number of grid intersections in the medial thigh area, as well as the total number of intersections crossed by a contrast-opacified artery were counted individually by a single observer blinded to the treatment regimen. An angiographic score was calculated for each film as the ratio of grid intersections crossed by opacified arteries divided by the total number of grid intersections in the medial thigh.

Immunohistochemistry and Determination of Capillary Density

The effect of cell transplantation (or saline injection) on neovascularization was assessed under light microscopy by measurement of the number of EC capillaries in sections taken from the ischemic muscles. Tissue specimens were obtained from the adductor and semimembranous muscles at day 35. These two muscles were chosen because they are the two principal muscles of the medial thigh, and each was originally perfused by the deep femoral artery that was ligated when the common/superficial femoral arteries were excised. Frozen sections 5 $\mu$m thick were prepared from each specimen so that the muscle fibers were oriented transversely. The sections were stained for AP to detect capillary ECs. Additional sections were stained for vWF to further confirm the EC phenotype. The capillary ECs were counted under light microscopy (X200) to determine the capillary density. Five fields from the two muscle samples of each animal were randomly selected for the capillary counts. To ensure that the capillary density was not overestimated as a consequence of myocyte atrophy or underestimated because of interstitial edema, the capillary/muscle fiber ratio was also determined.

Laser Doppler Blood Perfusion Analysis

At postoperative day 35, we evaluated blood flow of the ischemic thigh area using a laser Doppler blood perfusion image (LDPI) system (moorLDI, Moor Instruments) as described previously and incorporated herein by reference (Murohara et al. *J Clin Invest.* 1998;101:2967–2578). Low or no blood perfusion was displayed as dark blue, whereas the highest perfusion interval was displayed as red to white.

Results obtained from the studies described above are expressed as mean±SEM. Statistical significance of differences was analyzed among three experimental groups by ANOVA followed by Fisher's t test for comparison between any two groups. Statistical significance was assumed at a value of $P<0.05$. n represents the number of animals.

EPCs Developed From Rabbit BM-MNCs In Vitro

When isolated BM-MNCs (n=10) were cultured on fibronectin, a number of cell clusters appeared within 24 hours (FIG. 1a). Spindle-shaped and attaching (AT) cells then sprouted from the edge of the clusters within three days. AT cells formed linear cord-like structures (FIG. 1b) and multiple cell clusters (FIG. 1c). These clusters fused with each other to form a larger cell monolayer (FIG. 1c), which then turned into network structures (FIG. 1d).

AT cells observed after seven days of culture were positively stained for both Ulex lectin binding (FIG. 1e) and vWF expression (FIG. 1f), characteristic markers of ECs. More than 80% of the AT cells took up DiI-acLDL (FIG. 1g and 1h), one of the characteristic functions of ECs. (Garlanda and Dejana *Arterioscler. Thromb. Vacs. BioL* 1997;17:1193–1202) AT cells having the ability to incorporate DiI-acLDL also released NO in the presence of L-arginine 1 mmol/L, as assessed by DAF-2 DA, an NO-specific fluorescent indicator (FIG. 1i). Thus, AT cells had multiple EC characteristics and the AT cells were defined as a major population of EPCs.

Figures 2A, 2B, 2C, 2D, 2E, 2F:
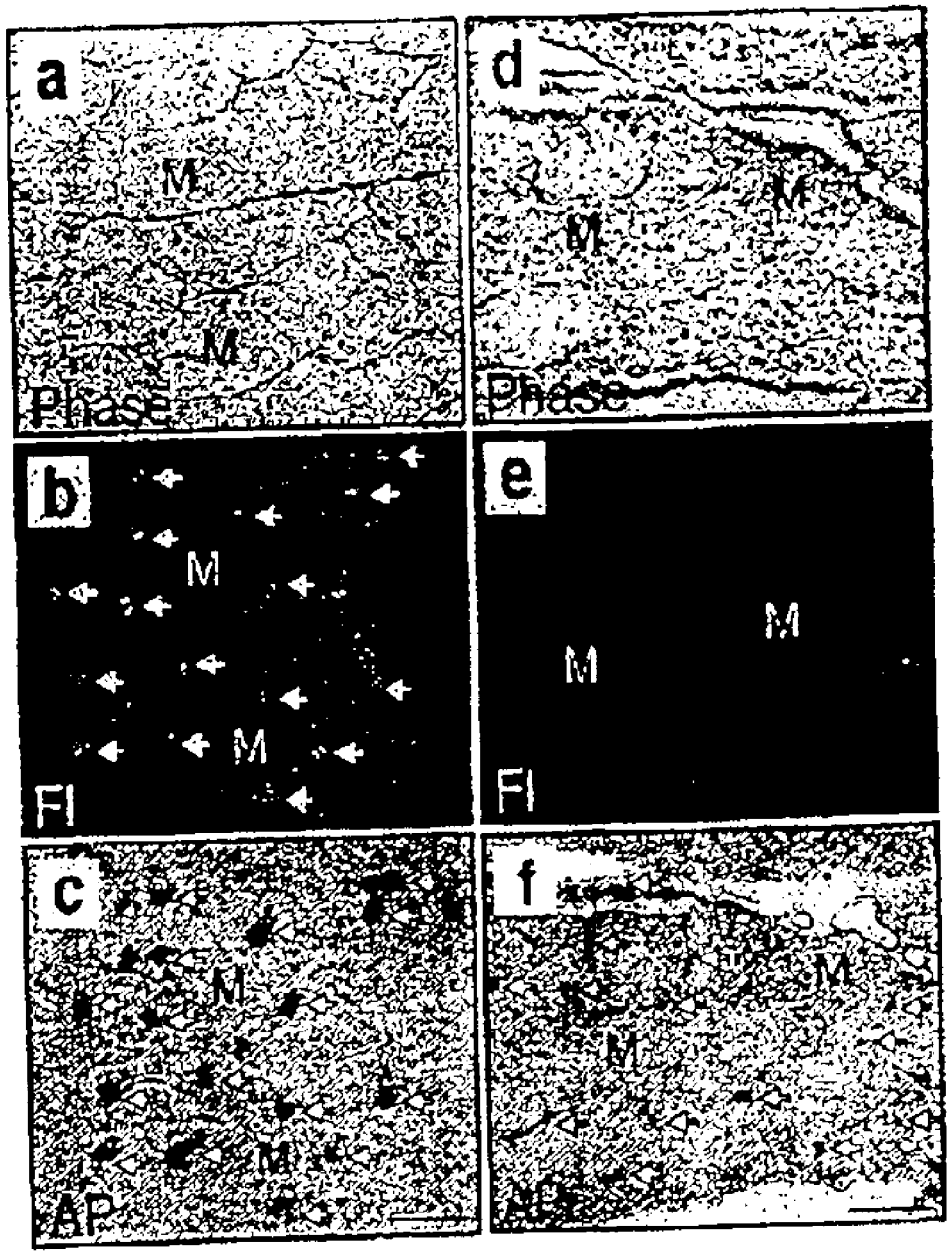
FIGS. 2a–2f. Transplanted autologous BM-MNCs survived and participated in formation of capillary structures in vivo.

Transplanted Autologous BM-MNCs, But Not BM-Fibroblasts Participated in Neovascular Formation in Ischemic Tissues Two weeks after transplantation of fluorescence-labeled BM-MNCs (n=8), fluorescence microscopic examination of frozen sections prepared from the ischemic tissues disclosed that transplanted BM-MNCs were incorporated into the EC capillary networks among the preserved skeletal myocytes (FIGS. 2a and 2b). In adjacent frozen sections, most of the fluorescence-positive cells were costained with AP, an enzyme within intact capillary ECs, indicating that the transplanted BM-MNCs had survived and had participated in the formation of a capillary network (FIGS. 2b and 2c).

As a control experiment, transplanted autologous BM-fibroblasts (n=15) were studied to determine whether they participated in neovascular formation in the ischemic tissues. Examination of multiple frozen sections obtained two weeks after transplantation revealed that there were almost no fluorescence-positive cells in the ischemic tissues (FIGS. 2d and 2e). There was discrepancy in the spatial distribution between fluorescence-positive cells (BM-fibroblasts) and AP-positive cells (capillary ECs) (FIGS. 2c and 2f), indicating that transplanted fibroblasts were not incorporated into the capillary structures.

Local Transplantation of Autologous BM-MNCs Augmented Neovascularization and Collateral Vessel Formation in Ischemic Hindlimb Local transplantation of autologous BM-MNCs and BM-fibroblasts was performed to determine whether such transplantation might augment angiogenesis and collateral vessel formation in the rabbit ischemic hindlimb in vivo. There were no significant differences in body weight or systolic blood pressure among the three experimental groups when examined immediately before cell transplantation (or saline injection in the control) and at postoperative day 35.

CBP Ratio

Figure 3:
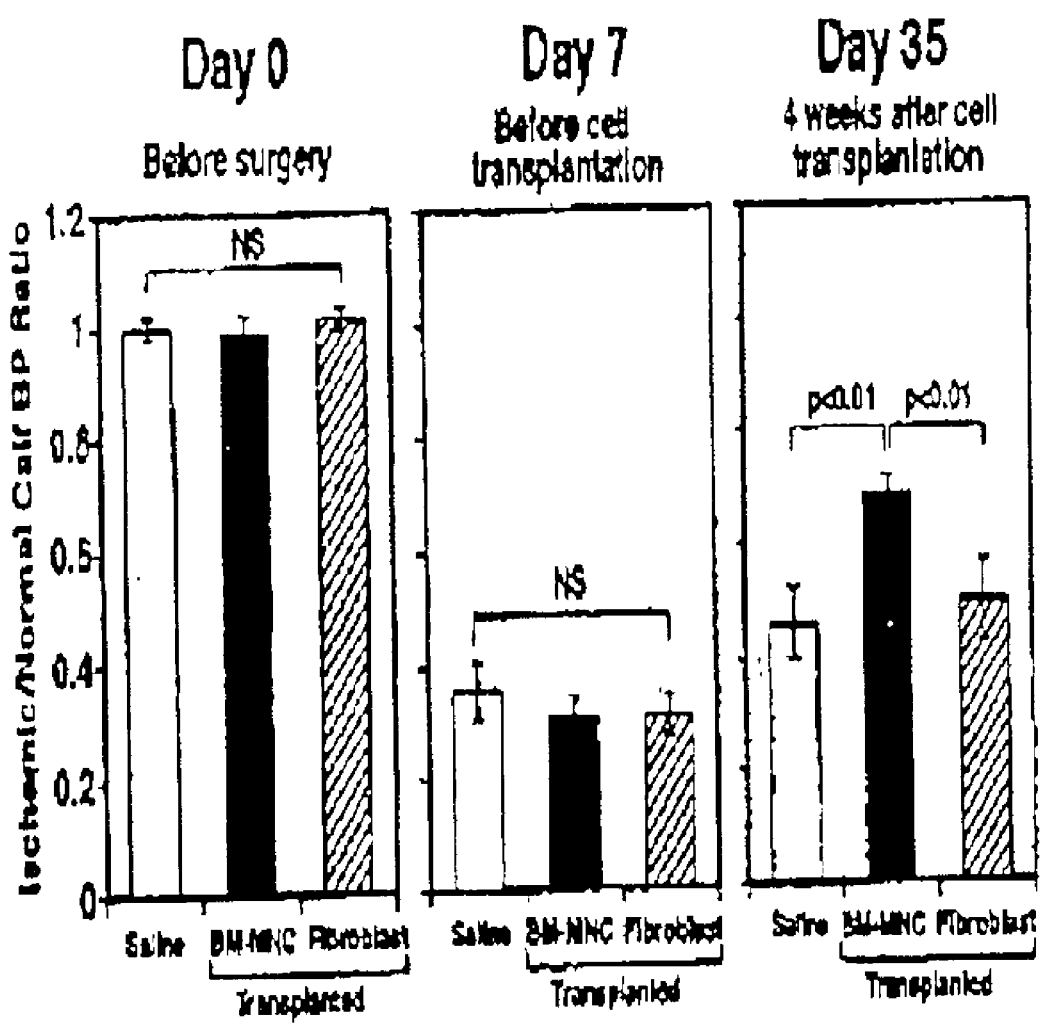
FIG. 3. Ratio of ischemic/normal limb CBP examined before limb ischemia (day 0), immediately before cell transplantation (day 7), and at postoperative day 35. There were no differences in CBP ratios among the 3 groups at days 0 and 7, indicating that the severity of limb ischemia was comparable among the 3 groups before cell transplantation. At postoperative day 35, however, CBP ratio was greater in the BM-MNC group than in the other 2 groups.

Before induction of limb ischemia and at postoperative day seven (i.e., before cell transplantation), there were no significant differences in the ischemic (left)/normal (right) CBP ratios among the three groups (FIG. 3), indicating that severity of limb ischemia was comparable among the three groups. At postoperative day 35 (28 days after cell transplantation), however, the CBP ratio was significantly greater in the BM-MNC group than in the other two groups (FIG. 3), indicating that collateral blood flow was enhanced only in the BM-MNC group.

Angiographic Score

Figures 4A, 4B:
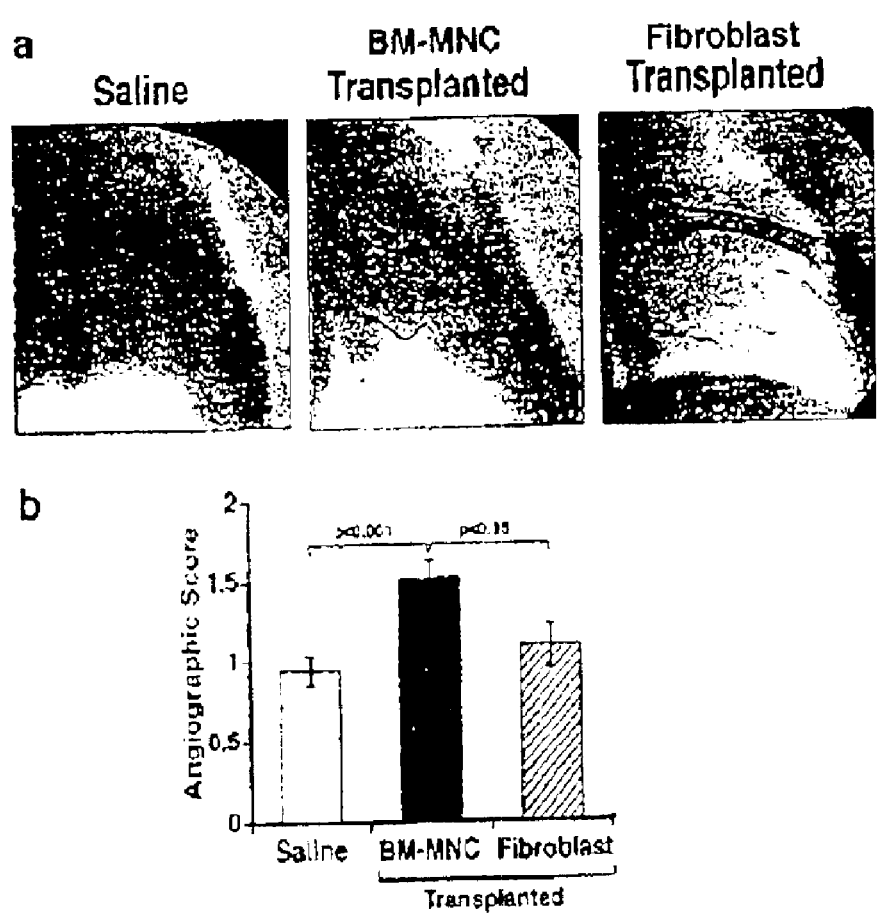
FIGS. 4a–4b. Representative angiograms obtained at postoperative day 35. In control and BM-fibroblast-transplanted animals, a moderate degree of collateral vessel formation was observed in the ischemic thigh area. Numerous collateral vessels were observed, however, in the BM-MNC-transplanted rabbit.

At postoperative day 35, all animals were subjected to iliac arteriography. Representative angiograms of the three groups are shown in FIG. 4a. Numerous collateral vessels developed in a BM-MNC-transplanted rabbit but not in control or BM-fibroblast-transplanted animals. Quantitative analyses using angiographic score showed a significantly greater number of collateral vessels in the BM-MNC group than in the other two groups at the ischemic tissues (FIG. 4b).

Capillary Density

Figures 5A, 5B:
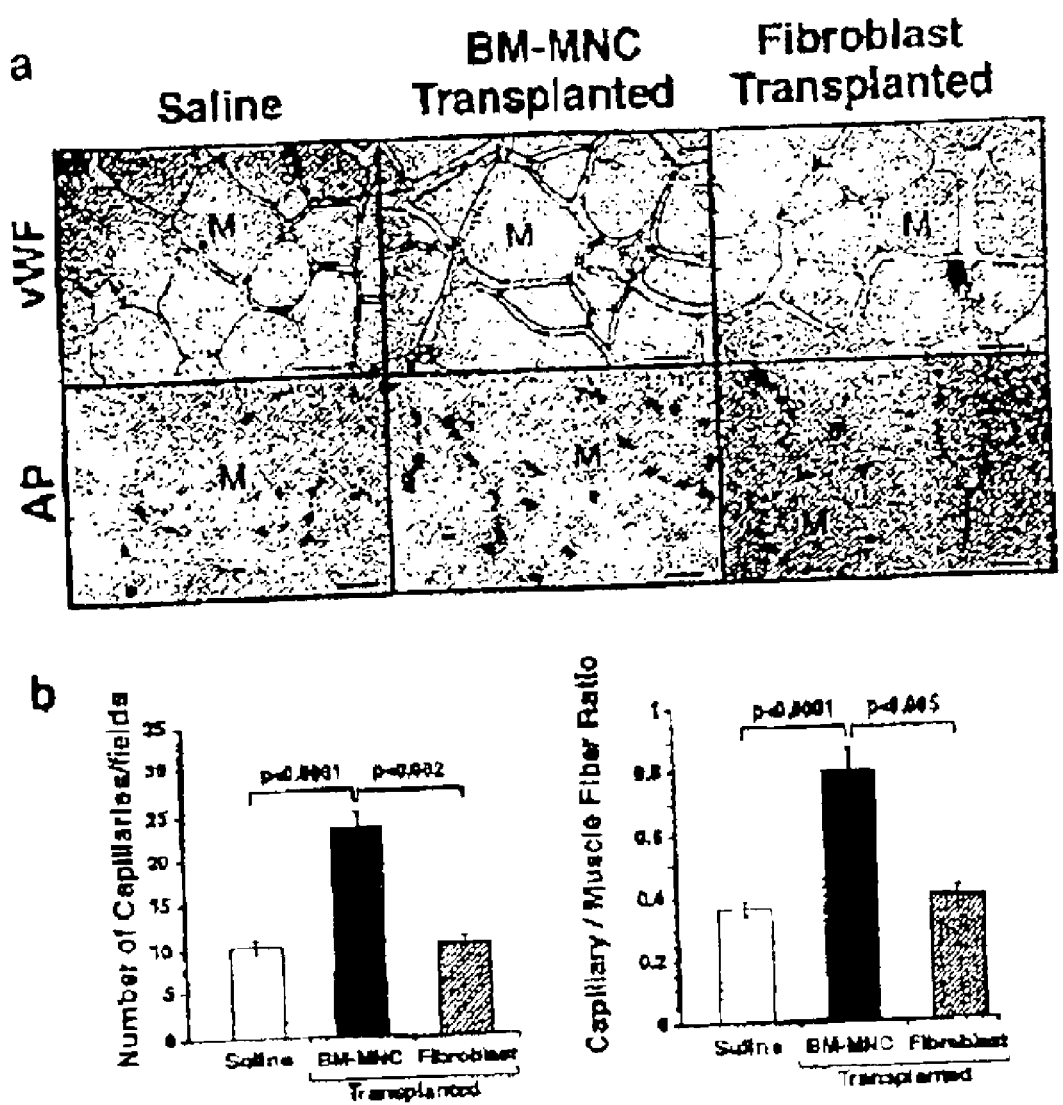
FIGS. 5a–5b.

Capillary density was calculated as the specific evidence of vascularization at the microvascular level. Representative photomicrographs of histological sections in the ischemic tissues are shown in FIG. 5a. Immunohistochemical staining for vWF and for AP revealed the presence of numerous capillary ECs in a BM-MNC transplanted rabbit, but a lower number of capillary ECs was seen in control and BM fibroblast-transplanted animals. Quantitative analyses revealed that the capillary density at the ischemic region was significantly higher in the BM-MNC group than in the other two groups (FIG. 5b). The capillary/muscle fiber ratio was also greater in the BM-MNC group than in the other two groups (FIG. 5b).

Laser Doppler Blood Perfusion

Figures 6A, 6B:
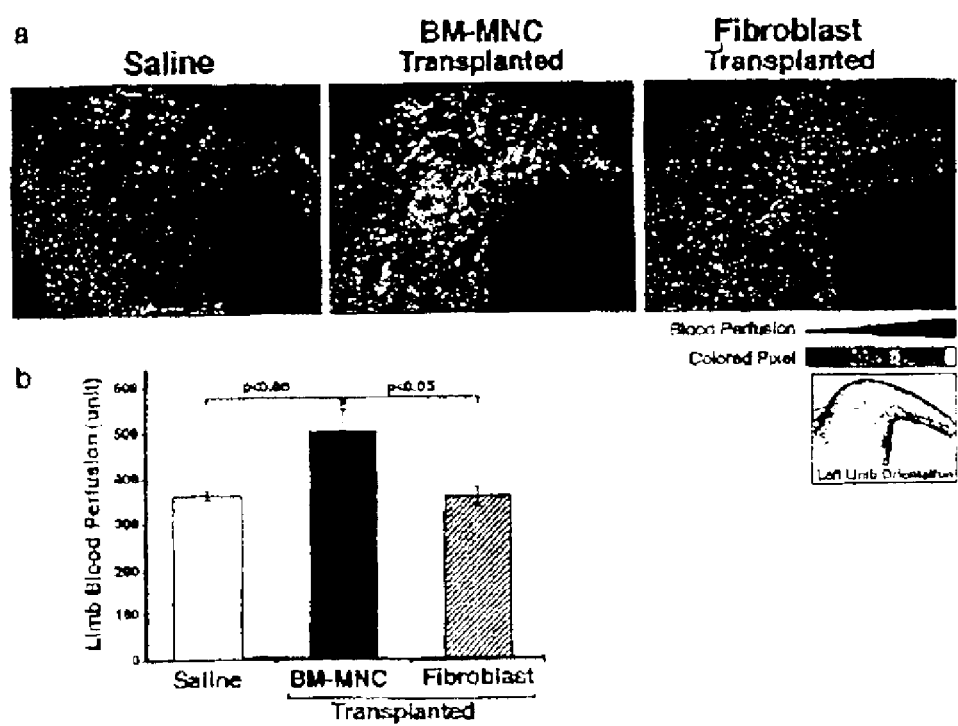
FIGS. 6a–6b.

To analyze subcutaneous blood perfusion in the ischemic hindlimb, LDPI analysis was performed. Representative images are shown in FIG. 6a. A greater degree of blood perfusion was observed in the ischemic limb (red to white color distribution) of a BM-MNC-transplanted rabbit than in control and BM-fibroblasttransplanted animals (blue to green colors). FIG. 6b summarizes the blood perfusion indexes calculated from LDPIs in the ischemic thigh region. Although marked recovery of blood perfusion was observed in the BM-MNC-transplanted group, blood flow remained low in the other two groups.

EXAMPLE 2

Therapeutic Angiogenesis by Bone Marrow-Derived Cell Transplantation in Pigs with Coronary Constrictor-Induced Chronic Myocardial Ischemia Previously it was shown that bone marrow-derived mononuclear cells (BM-MNCs) isolated from rabbits gave rise to functional endothelial progenitor cells (EPCs) that contributed to postnatal angiogenesis when injected into rabbit ischemic hindlimb. (Shintani et al. *Circulation* 2001; 103:897–903)

A pig model of chronic myocardial ischemia was used herein to test the hypothesis that functional EPCs develop from BM-MNCs. Using an endovascular approach, it is shown herein that local transplantation of autologous BM-MNCs augments neovascularization in response to tissue ischemia.

One month after ameroid constrictor placement around the left circumflex artery to produce ischemia, baseline measurements and treatment were performed. Animals (n=9) were injected with either saline (n=4) or autologous BM-MNCs (n=5) into the ischemic area using an intramyocardial injection catheter (Boston Scientific). BM-MNCs from the animals were isolated using a density-gradient centrifugation method. Each pig received 10 intramyocardial injections of 20 µl. Coronary angiography, dobutamine stress echocardiography and myocardial blood flow measurement using microsphere injection were performed at the time of treatment and after four weeks.

At follow-up, the filling rate of the artery distal to the ameroid occlusion was significantly improved in the treated group (from 15±14 to 4±7 frames;p<0.05), as well as the regional left ventricle wall motion score at peak stress (from 1.32±0.11 to 1.02±0.04, p<0.01). Additionally, the endocardial/epicardial ratio of myocardial blood flow in the ischemic region increased in the treatment group at follow-up (from 0.80±0.23 to 1.17±0.13, p=0.07). These results demonstrate that BM-MNCs transplantation increases blood flow at the treated site.

EXAMPLE 3

Therapeutic Angiogenesis by Bone Marrow-Derived Cell Transplantation in Pigs with Coronary Constrictor-Induced Chronic Myocardial Ischemia Recently, the impact of direct intramyocardial injection of angiogenic factors on collateral function has been reported not only in experimental studies, but also in patients during open-heart surgery. (Mack CA, et al. *J Thorac Cardiovasc Surg* 1998; 115:168–176; Schumacher B, et al. *Circulation* 1998; 97: 645–650; Losordo DW, et al. *Circulation* 1998 98: 2800–2804) Moreover, the feasibility of various catheter-based systems for catheter-based intramyocardial injection of marker genes has been demonstrated in animal models. (Vale P R, et al. *J Am Coll Cardiol* 1999;34:246–54) The next logical step in development and testing of this potential new therapy for chronic myocardial ischemia is application in a large-animal preparation using a technically feasible catheter-based approach.

Accordingly, the methods of the present invention tested the hypothesis that local transplantation of autologous BM-MNCs may augment neovascularization in response to tissue ischemia using a porcine model of chronic myocardial ischemia. Example 3 presents the same study as Example 2 except additional animals are included.

All experiments and animal care conformed to the National Institute of Health and American Heart Association guidelines for the care and use of animals and were approved by the Institutional Animal Care and Use Committee of the Atlanta Cardiovascular Research Institute.

Porcine Model of Chronic Myocardial Ischemia

Domestic farm pigs weighing ~20–25 kg were sedated with intramuscular injection of telazol (5 mg/kg), intubated, and anesthetized with isoflurane inhalation. With the pigs under anesthesia and given mechanical ventilatory support, an ameroid constrictor was placed around the proximal LCX just distal to the main stem of the left coronary artery matching the size of the vessel (typically 1.75, 2.00, 2.25 mm ID), through the 4$^{th}$ left intercostal space. The chest was closed and the animal allowed to recover. One month later, pigs received baseline measurements and were randomized to receive BM-MNCs or sham injection (saline, controls) into the ischemic myocardium. The pigs recovered and at one month after treatment, underwent repeat angiographic, hemodynamic, and echocardiographic assessment. Myocardial samples were taken from ischemic and adjacent normal areas for assessment of regional blood flow by the microsphere technique and capillary density by histomorphometry.

BM-MNCs Isolation

From the iliac crest 50 ml of BM was aspirated and anticoagulated with citrate. BM-MNCs were isolated using a density-gradient centrifugation method as described previously and hereby incorporated by references. (Shintani et al. *Circulation* 2001; 103:897–903; Mack C A, et al. *J Thorac Cardiovasc Surg* 1998; 115:168–176)

BM-MNCs Transplantation to Ischemic Myocardium.

Two groups of pigs received intracavitary left ventricular myocardial injection of either BM-MNCs (n=6) or saline (n=6) one month after implantation of an ameroid constrictor around the left circumflex coronary artery, using a myocardial injection catheter (Stilletto™, Boston Scientific Inc., Boston, Mass., FIG. A). The injection catheter was introduced through #7 F Steering Guide and #9 F LV sheath a femoral artery access. Stiletto was advanced to the endocardial wall under fluoroscopy and ECG monitoring. The shaft was loaded against the wall, which was evident by a slight prolaps of the shaft, and/or guide back-out. Ventricular premature contraction was often observed during this procedure.

Cell Culture

Medium-199 with 20% fetal bovine serum, endothelial cell growth supplement and antibiotics was used for all cell culture experiments. BM-MNCs were cultured on gelatin-coated plastic plates at 37° C. in a humidified incubator supplied with 5% $CO_2$/95% air.

Left Ventricular Wall Motion Study

Left ventricular wall motion was evaluated by dobutamine stress echocardiography at the time of and one month after BM-MNCs transplantation or saline injection.

Dobutamine Stress Echocardiography

Dobutamine stress echocardiography was performed in ~3 minute stages with incremental doses of dobutamine beginning with ~2.5 µg/kg/min and increasing to 40 µg/kg/min. Based on a 10 segment model (6 segments in short axis view at papillary muscle level, 4 segments in long axis view), wall motion was graded as 1=normal, 2=hypokinetic, 3=akinetic, or 4=dyskinetic. The regional wall motion score was calculated at rest, low dose (less than 5.0 µg/kg/min of dobutamine), and peak stress. The echocardiograms were interpreted by experienced observers unaware of treatment assignment.

Coronary Angiography

Formation of collateral vessels was evaluated by coronary angiography at the time of and one month after BM-MNCs transplantation. Angiography was performed on the right and left coronary artery in orthogonal LAO and RAO projections.

Evaluation was performed through cinefilm review by two experienced angiographers unaware of treatment assignment. A collateral score was established in each film based on the classification proposed by Rentrop and colleagues which is hereby incorporated by reference. (Rentrop K P et al. *J Am Coll Cardiol.* 1985; 5: 587–92) In brief, collaterals were graded as absent (0), filling of side-branches of a target occluded epicardial coronary artery via collaterals without visualization of the epicardial coronary artery itself (1+), partial filling of the epicardial segment via collateral arteries (2+), complete filling of the epicardial segment (3+).

Measurement of Myocardial Flow

Myocardial blood flow at baseline and one month after BM-MNC or sham injection was measured using gold- and samarium-containing microspheres (BioPhysics Assay Laboratory Inc., Wellesley Hills, Mass.) using modifications of previously described techniques of Reinhardt CP et al. *Am. J. Physiol Heart Circ. Physiol* 280:H108–H116 (2001), which are hereby incorporated by reference. Briefly, microspheres were injected into the left atrium by retrograde catheterization from the femoral artery, using a #6F multipurpose catheter. The position of the catheter was verified under fluoroscopy and ~5 million red (gold-containing, for evaluation of baseline flow) or black (samarium-containing, for evaluation of flow one month after treatment) microspheres were injected into the left atrium as a bolus, followed by flush with 10 ml sterile saline solution. Five seconds before microsphere injection withdrawal of a reference blood sample was initiated from the femoral artery introducer sheath using a syringe pump; this continued for two minutes at a rate of 5 ml/min. Post sacrifice, the heart was removed and transmural tissue samples of ~1 cm width were cut from the ischemic (LCX territory) and normal (LAD territory) left ventricular free wall. These samples were then cut into six radial segments and further subdivided into epicardial and endocardial regions. The number of microspheres was obtained using neutron activation in vitro to yield for tissue, the number of microsphere/mg tissue and for blood, the number of microspheres/ml. Average myocardial blood flow in the three regions at baseline and follow-up was then calculated using the following formula:

MBF in tissue sample, ml/min/g=[syringe pump withdrawal rate (10 ml/2 min)/tissue sample weight, g]×[# microspheres in tissue/# microspheres in reference blood sample]

Immunohistochemistry and Determination of Capillary Density

The impact of transplantation of autologous BM-MNCs on myocardial vascularity at one month was assessed by a single observer unaware of treatment assignment, using light microscopic planimetric morphometry. The number and crosssectional density of capillaries was measured in sections stained for factor VIII-related antigen (vWf) by indirect immunocytochemistry using the avidin-biotin complex technique, with alkaline phosphatase as the secondary antibody-conjugated chromogenic enzyme and Vector Red as the substrate, and counterstained with Gill's hematoxylin. Ten each microscopic fields (400×instrument magnification) from sections cut perpendicular to the long axis of the cardiac muscle fibers, from LCX ischemic region and LAD adjacent normal region were acquired and digitized. The total number of capillaries as defined by size and shape (roughly circular profiles<50 µm) and vWf reactivity in each field were counted using an image processing function (Image Pro Plus, Media Cybernetics, Rockville, Md.). The capillary density (number/mm$^2$) was calculated.

Identification of Transplanted BM-MNCs in Ischemic Tissue

Three additional pigs underwent ameroid constrictor implantation and at two weeks autologous BM-MNCs were isolated and labeled with a red fluorescent marker, PKH26-Red (Sigma). Labeled BM-MNCs were then transplanted into the ischemic myocardium using same myocardial injection catheter procedure. At 14 days after transplantation, pigs were euthanized with an overdose of potassium chloride and 16 pieces of ischemic tissue per animal were obtained. Multiple frozen sections 5 $\mu$m thick were prepared and also stained for DAPI, a DNA fluorescent dye and examined under a fluorescence microscope to examine whether transplanted BM-MNCs survived in the tissue.

Statistical Analysis

All values are expressed as mean ±SD. Between-groups comparisons were made using Student's t test (paired or unpaired as appropriate). One-way ANOVA followed by Fisher's t test was used when comparing $\geq 3$ groups. A critical value of $P<0.05$ was considered to indicate a significant difference or treatment effect.

EPCs Develop From Porcine BM-MNCs In Vitro

Figures 7A, 7B, 7C:
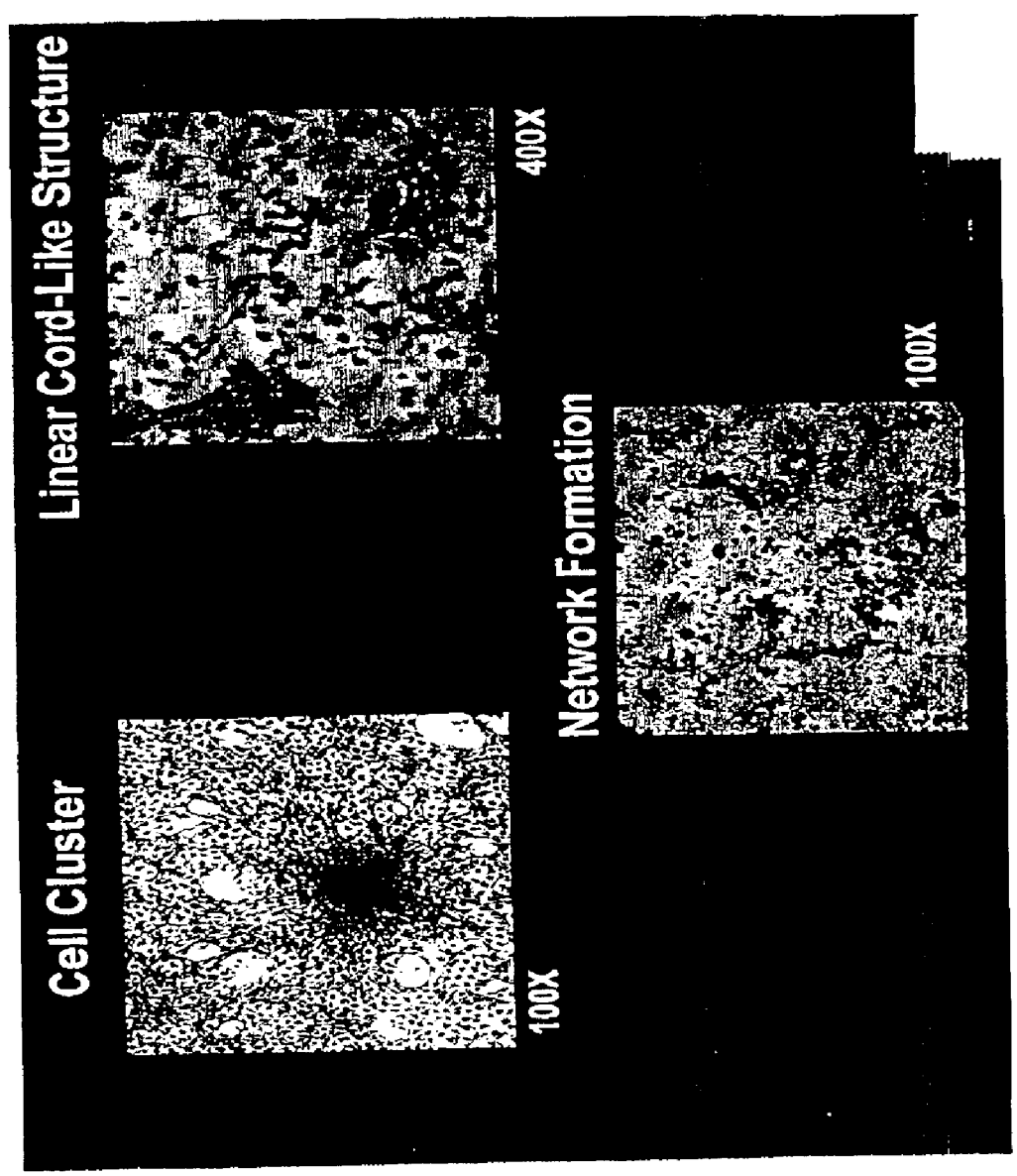
FIGS. 7a–7c. EPCs develop from porcine BM-MNCs in vitro. BM-MNCs cultured on gelatin-coated plates developed into attached cells and spindle-shaped cells (FIG. 7a, 100×) which formed linear cord-like structures and multiple cell clusters which appeared in 14 days (FIG. 7b,400×); cell clusters fused to form a larger cell monolayer that formed network structures (FIG. 7c, 100×).

When BM-MNCs were cultured on gelatin-coated plastic plates, attached and spread or spindle-shaped cells formed linear cord-like structures and multiple cell clusters which appeared within 14 days (FIGS. 7a–7c), as in a previous study. (Shintani S, et al. *Circulation* 2001; 103:897–903)

Catheter-Based Injections

Four pigs were tested to find the localization of catheter-based injections with 20 $\mu$l methylene blue. Injection sites of methylene blue staining were identified at necropsy in each heart. Success rate was 85+13% to localize injections sites in the postero-lateral left ventricular myocardium. Hemorrhagic pericardial effusion or methylene blue-contaminated effusion was not observed in any heart.

In the treatment group, each pig received ~8.0±1.5×10$^8$ BM-MNCs in ten 20 $\mu$l injections into the ischemic, postero-lateral left ventricular free wall using the myocardial injection catheter. Controls received ten 20 $\mu$l injections of sterile saline solution.

Coronary Angiography

At the time of and one month after BM-MNCs transplantation or saline injection, pigs underwent coronary angiography. There was no difference in stenosis of the LCX at the site of ameroid constrictor placement between the groups at baseline (92±11% vs. 94±11, treatment group vs. control) or at follow-up (96±9% vs. 95±9, respectively).

Collateral angiograms with Rentrop score>1+were observed in 2 pigs from the control and 1 pigs from the BM-MNCs group before treatment. At follow-up, 5 out of 6 pigs from the treatment group showed collateral vessels formation>1+, compared to 4 out of 6 pigs from the control group Dobutamine Stress Echocardiography Average regional wall motion score both at rest and under stress at the baseline time point was not different between the control and treatment groups, indicating that the decrement in the left ventricular function induced by ameroid constrictor stenosis was comparable between the groups before treatment (FIG. 8a).

Figures 8A, 8B:
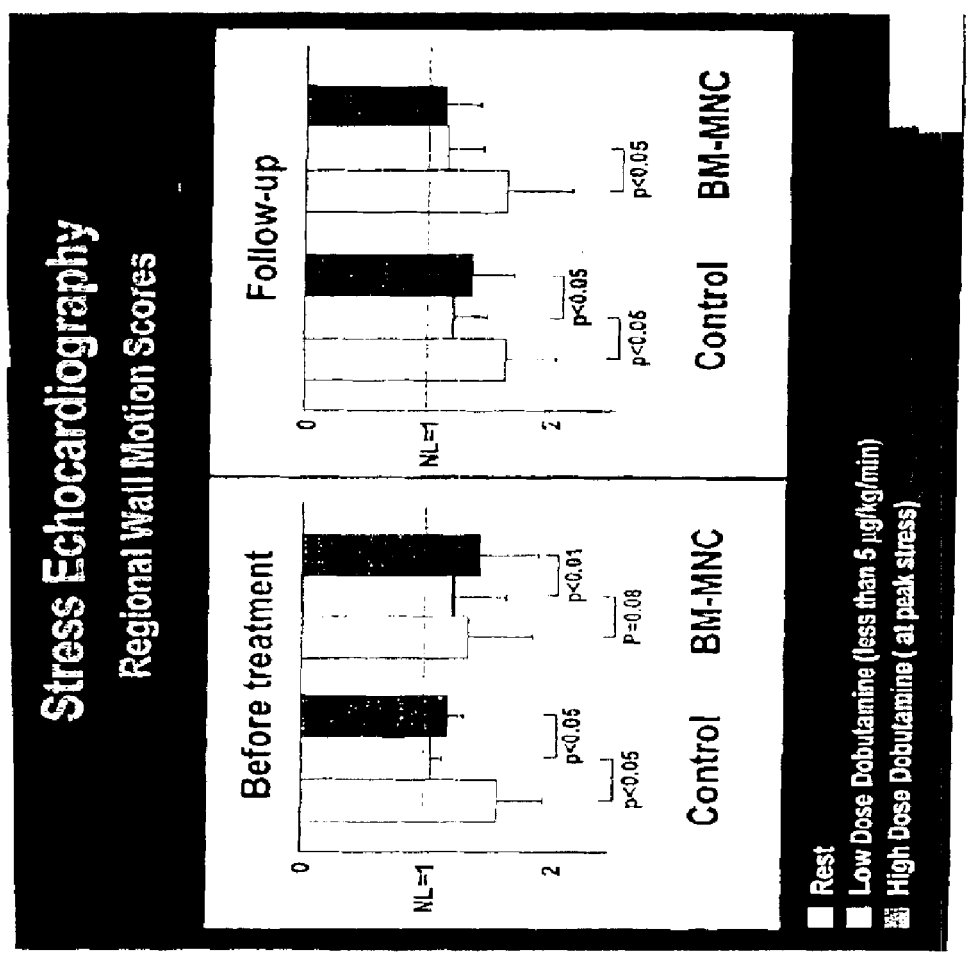
FIGS. 8a–8b. Stress Echocardiography Regional wall Motion Scores. Average regional wall motion score both at rest and under stress at the baseline, i.e. rest, was not different between the control and treatment groups (FIG. 8a). At one month post treatment, the hypokinesis observed when increasing from low-dose to high-dose pharmacologic stress was still present in controls whereas there was no difference in wall motion between low and high dose dobutamine for pigs given BM-MNCs at the time of treatment (FIG. 8b). The BM-MNC treated pigs showed a significant improvement in high-dose dobutamine experiments after treatment (FIG. 8b) at follow-up as compared to before treatment (1.02+/−0.04 vs. 1.27+/−0.16; p<0.020).

At one month post treatment, the hypokinesis observed when increasing from low-dose to high-dose pharmacologic stress was still present in controls whereas there was no difference in wall motion between low and high dose dobutamine for pigs given BM-MNCs at the time of treatment (FIG. 8b). The BM-MNC treated pigs showed a significant improvement in high-dose dobutamine experiments after treatment (FIG. 8b) at follow-up as compared to before treatment (1.02+/−0.04 vs. 1.27 +/−0.16; p<0.020).

Myocardial Blood Flow

Figure 9:
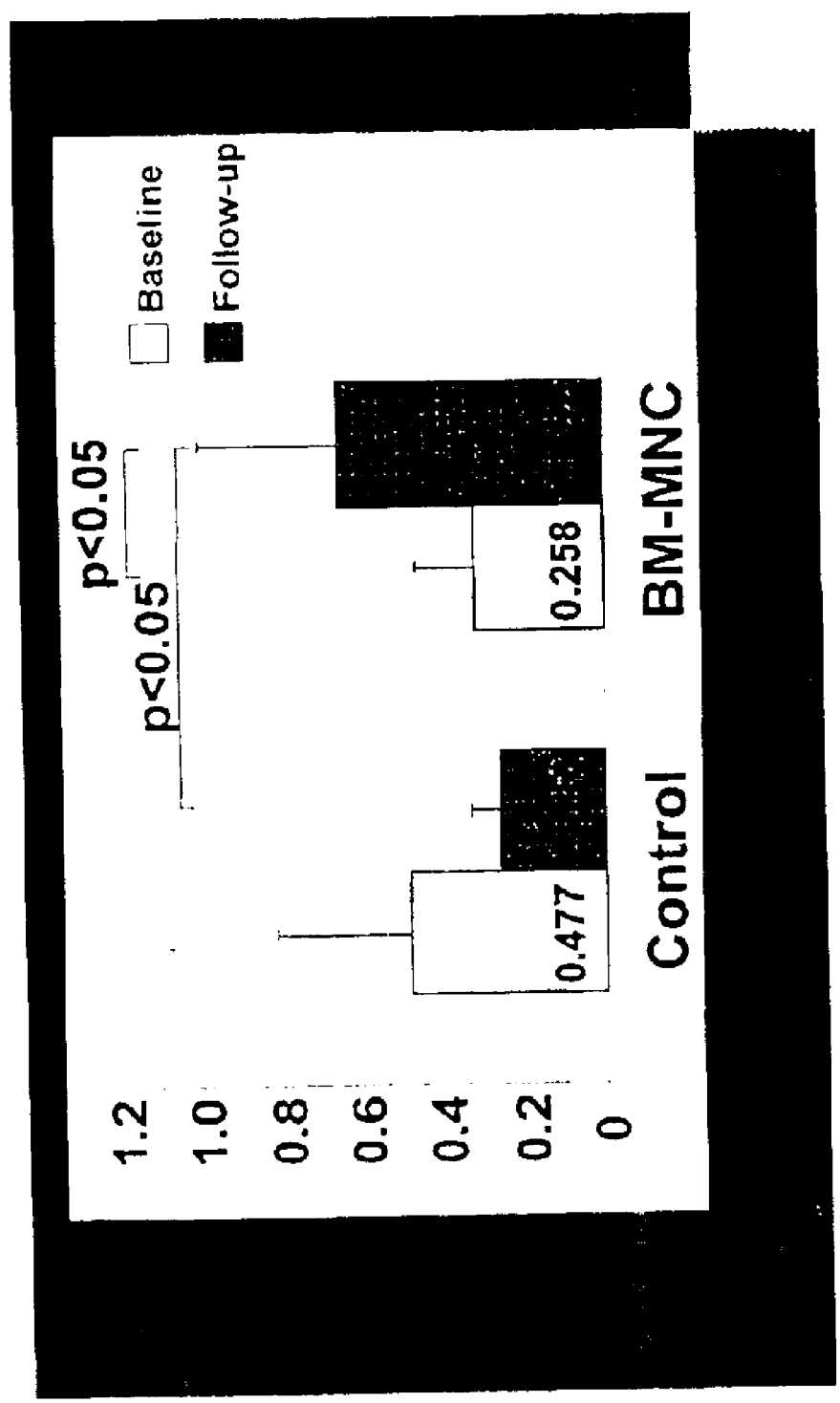
FIG. 9. Transmural Myocardial Blood Flow in Ischemic Area. Before treatment, there were no significant differences in myocardial blood flow between the two groups, Control and BM-MNCs transplanted group. At one month after treatment, however, myocardial flow was significantly increased only in the BM-MNCs group compared to the baseline value (0.31±0.14 vs. 0.65±0.35 ml/min/g, P<0.05), and was also significantly greater in the BM-MNCs group compared to controls.

Before treatment, there were no significant differences in myocardial blood flow between the two groups. At one month after treatment, however, myocardial flow was significantly increased only in the BM-MNCs group compared to the baseline value (0.31±0,14 vs. 0.65±0.35 ml/min/g, P<0.05), and was also significantly greater in the BM-MNCs group compared to controls. (FIG. 9)

Capillary Density

Figures 10A, 10B:
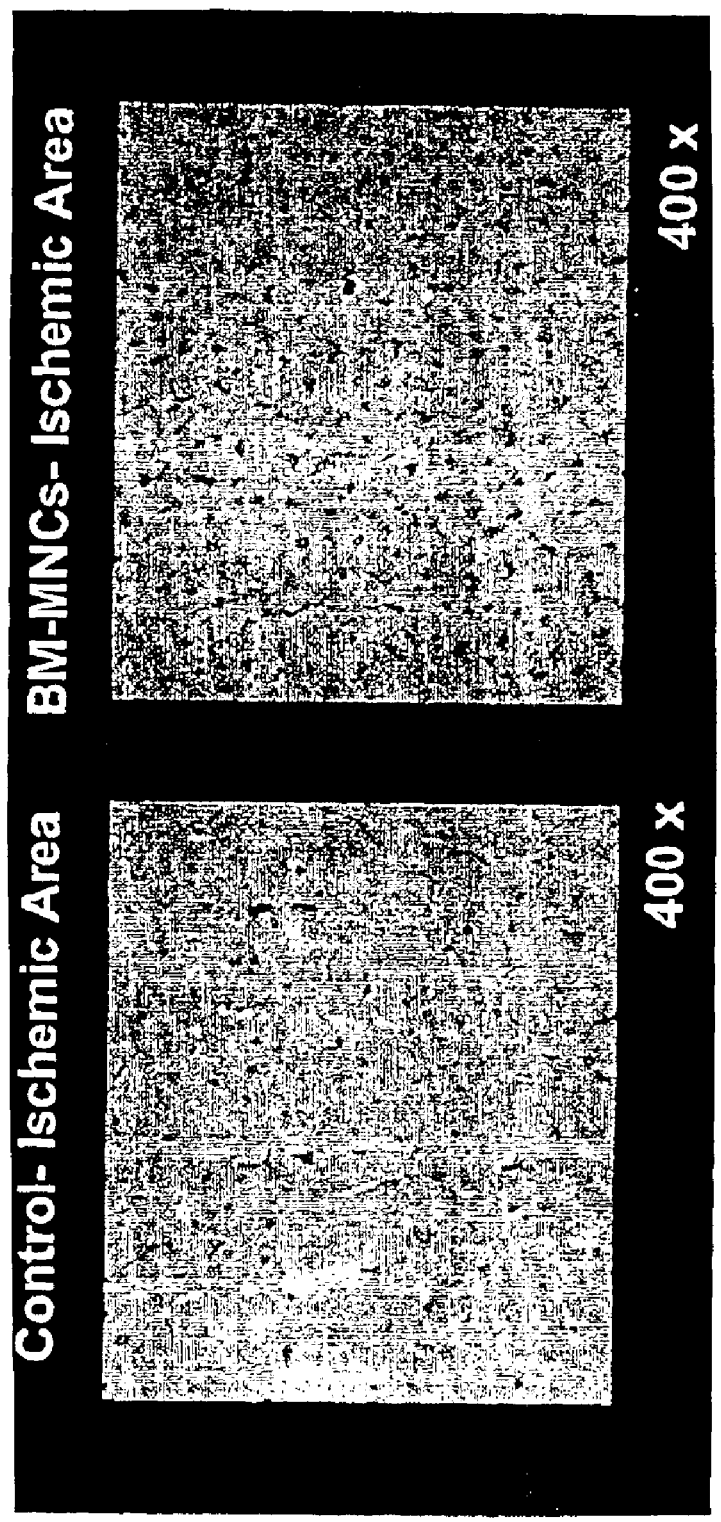
FIGS. 10a–10b. Factor VIII-Related Antigen (von Willebrand Factor) Immunocytochemistry. Representative photomicrograms of histologic sections from ischemic myocardium: Control Ischemia Area, 400×(FIG. 10a) and BM-MNCs-Ischemic Area, 400×(FIG. 10b).

Tissue sections from the myocardium were examined histologically as described above. Representative photomicrograms of histologic sections from ischemic myocardium are shown in FIGS. 10a and 10b. Quantitative analysis revealed that the capillary density was significantly higher in the ischemic area from pigs treated with BM-MNCs (1854±279/mm$^2$) than in the ischemic area from pigs injected with saline (1292±347/mm$^2$).

Detection of Transplanted Autologous BM-MNCs In Ischemic Myocardium

Figures 11A, 11B, 11C:
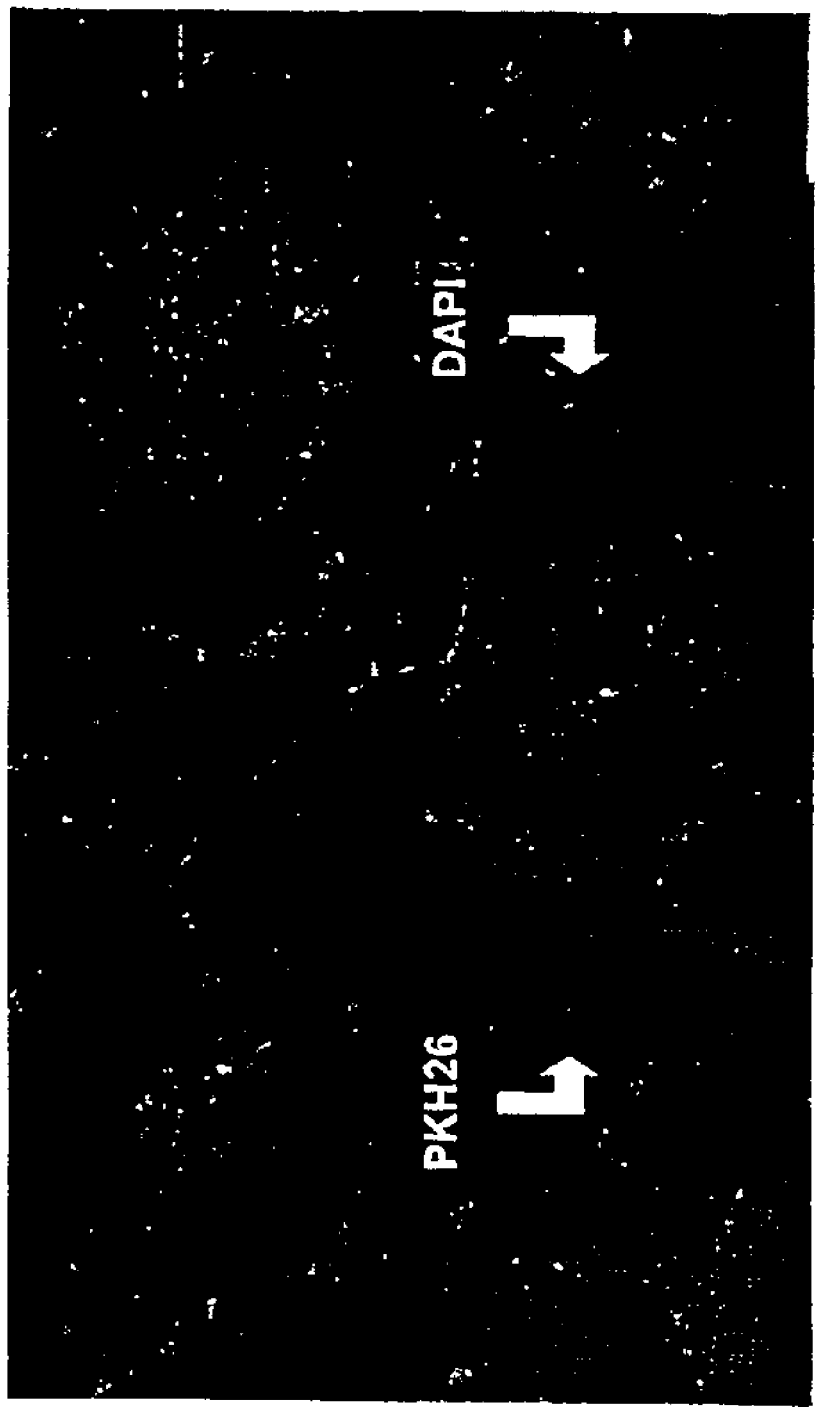
FIGS. 11a–11c. PKH26 and DAPI Staining of Porcine Myocardium Two Weeks after BM-MNCs Transplantation. PKH26 (FIG. 1a), DAPI (FIG. 11b), and PKH26 and DAPI Staining (FIG. 11c).

The transplanted cells survived after 2 weeks in the sites of injection suggesting that the PKH labeling technique as well as the catheter-based injection technique were successful (FIG. 11a–11c). The results demonstrate that BM-INC participate in the neovascularization process.

The present invention demonstrates that autologous BM-MNCs are successfully transferred into ischemic myocardium and that these cells survived, and augmented neovascularization and myocardial blood flow. Moreover improvement of cardiac function in response to pharmacologic stress was confirmed after BM-MNCs transplantation. Thus, transplantation of autologous BM-MNCs promotes neovascular formation in the ischemic myocardium and this is related to enhanced functional recovery from ameroid induced myocardial ischemia.

BM-MNCs were transplanted without purification of endothelial progenitor cells in the methods of the present invention. Although CD34 and KDR were previously used as landmark molecules to isolate human EPCs (Asahara T, et al. *Science*. 1997;275:964–967; Murohara T, et al. *J Clin Invest*. 2000; 105:1527–1536), it was recently reported that coculture of human CD34+ and CD34− MNCs yielded a greater number of EPCs than culture of CD34+ alone. Additionally, previous in vitro 5 study showed that EPCs developed from rabbit BM-MNCs as well as human umbilical cord blood. (Murohara T, et al. *J Clin Invest*. 2000; 105:1527–1536; Shintani S, et al. *Circulation* 2001; 103:897–903) Moreover, there are no specific antibodies for CD34 in pigs currently available. Nevertheless, during culture, porcine BM-MNCs gave rise to linear-cord like as well as network structures, which were similar to those created by human and rabbit EPCs in previous studies. (Asahara T, et al. *Science*. 1997;275:964–967; Murohara T, et al. *J Clin Invest*. 2000; 105:1527–1536; Shintani S, et al. *Circulation* 2001; 103:897–903).

In the present invention, autologous BM-MNCs were transplanted locally using catheter-based needle injection. Catheter-based transendocardial local delivery may provide identical benefit without the need for surgery, and shows an retention of the injected contents in the host myocardium compared to transepicardial injection by a surgical approach. (Grossman PM, et al. *J Am Coll Cardiol*. 1999;35 (suppl A):870–1. Abstract) In a previous study, intravenously transfused EPCs participated in neovascularization in ischemic tissue in adult experimental animals. However, systemic intravenous delivery of angiogenic factors may evoke latent adverse effects in other tissues susceptible to or related to angiogenic disorders such as tumors or microvasculopathies. (Folkman J. *Nature Med*. 1995;1:27–3) Local delivery may avoid the potential systemic side effects of angiogenic cells or molecules as compared to systemic infusion.

In summary, transplantation of autologous BM-MNCs gave rise to neovascularization in the porcine chronic ischemic myocardium and consequently cardiac function was improved. The present invention supports the clinical use of autologous transplantations of BM-MNCs as a therapeutic strategy for patients with coronary heart disease who are not candidates for PTCA or CABG, and that such transplantation possesses certain advantages.

The foregoing description and examples detail specific methods which may be employed to practice the present invention. One of skill in the art will readily know and appreciate how to devise alternative reliable methods at arriving at the same information by using and/or modifying the disclosure of the present invention using ordinary skill. However, the foregoing description and examples should not be construed as limiting the overall scope of the present invention, but are to be considered as illustrative thereof. All documents and publications cited herein are expressly incorporated by reference into the subject application.

We claim:

1. A method of forming new blood vessels in cardiac muscle tissue in a subject, wherein the subject is a human, which comprises:
    a) isolating autologous bone marrow-mononuclear cells from the human, wherein the autologous bone marrow-mononuclear cells are isolated from bone marrow; and
    b) transplanting locally into the cardiac muscle tissue an effective amount of the autologous bone-marrow mononuclear cells, resulting in formation of new blood vessels in the cardiac muscle tissue.

2. The method of claim 1, wherein the new blood vessels comprise capillaries.

3. The method of claim 1, wherein the new blood vessels comprise collateral vessels.

4. The method of claim 1, wherein the cardiac muscle tissue is ischemic cardiac muscle tissue.

5. The method of claim 1, wherein the cardiac muscle tissue is damaged cardiac muscle tissue.

6. The method of claim 5, wherein the damaged cardiac muscle tissue is an artificially created site.

7. A method of increasing blood flow to cardiac muscle tissue in a subject, wherein the subject is a human, which comprises:
    a) isolating autologous bone-marrow mononuclear cells from the human, wherein the autologous bone marrow-mononuclear cells are isolated from bone marrow; and
    b) transplanting locally into the cardiac muscle tissue an effective amount of the autologous bone-marrow mononuclear cells so as to result in formation of new blood vessels in the cardiac muscle tissue, thereby increasing the blood flow to the cardiac muscle tissue in the human.

8. The method of claim 7, wherein the new blood vessels comprise capillaries.

9. The method of claim 7, wherein the new blood vessels comprise collateral blood vessels.

10. The method of claim 7, wherein the cardiac muscle tissue is ischemic cardiac muscle tissue.

11. The method of claim 7, wherein the cardiac muscle tissue is damaged cardiac muscle tissue.

12. The method of claim 11, wherein the damaged cardiac muscle tissue is an artificially created site.

13. A method of treating diseased cardiac muscle tissue in a subject, wherein the subject is a human, which comprises:
    a) isolating autologous bone-marrow mononuclear cells from the human, wherein the autologous bone marrow-mononuclear cells are isolated from bone marrow; and
    b) transplanting locally into the diseased cardiac muscle tissue an effective amount of the autologous bone-marrow mononuclear cells so as to result in formation of new blood vessels, thereby treating the diseased cardiac muscle tissue in the human.

14. The method of claim 13, wherein the diseased cardiac muscle tissue is ischemic cardiac muscle tissue.

15. The method of claim 13, wherein the new blood vessels comprise capillaries.

16. The method of claim 13, wherein the new blood vessels comprise collateral blood vessels.

17. A method of increasing angiogenesis in diseased cardiac muscle tissue in a subject, wherein the subject is a human, which comprises:
    a) isolating autologous bone-marrow mononuclear cells from the human, wherein the autologous bone marrow-mononuclear cells are isolated from bone marrow; and
    b) transplanting locally into the diseased cardiac muscle tissue an effective amount of the autologous bone-marrow mononuclear cells, thereby increasing angiogenesis in the diseased cardiac muscle tissue in the human.

18. The method of claim 17, wherein the diseased cardiac muscle tissue is ischemic cardiac muscle tissue.

19. A method of treating heart failure in a mammal, wherein the subject is a human, which comprises:
    a) isolating autologous bone-marrow mononuclear cells from the human, wherein the autologous bone marrow-mononuclear cells are isolated from bone marrow; and
    b) transplanting locally into the heart an effective amount of the autologous bone-marrow mononuclear cells so as to result in formation of new blood vessels, thereby treating heart failure in the human.

20. The method of claim 19, wherein the new blood vessels comprise capillaries.

21. The method of claim 19, wherein the new blood vessels comprise collateral blood vessels.

* * * * *

UNITED STATES PATENT AND TRADEMARK OFFICE
CERTIFICATE OF CORRECTION

PATENT NO. : 6,878,371 B2
DATED : April 12, 2005
INVENTOR(S) : Ueno et al.

It is certified that error appears in the above-identified patent and that said Letters Patent is hereby corrected as shown below:

Column 6,
Line 46, change "underperfised" to -- underperfused --.

Column 7,
Line 63, delete "15".

Column 9,
Line 30, change "angiogen is" to -- angiogenesis --.

Column 14,
Line 27, change "ischernia" to -- ischemia --.

Column 20,
Line 49, change "crosssectional" to -- cross-sectional --.

Signed and Sealed this

Twentieth Day of September, 2005

JON W. DUDAS
*Director of the United States Patent and Trademark Office*